(12) United States Patent
Hopkins

(10) Patent No.: US 10,925,658 B2
(45) Date of Patent: Feb. 23, 2021

(54) GUIDE WIRE ALIGNMENT

(71) Applicant: Zimmer, Inc., Warsaw, IN (US)

(72) Inventor: Andrew Rolfe Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 7 days.

(21) Appl. No.: 15/956,494

(22) Filed: Apr. 18, 2018

(65) Prior Publication Data

US 2018/0303533 A1 Oct. 25, 2018

Related U.S. Application Data

(60) Provisional application No. 62/488,472, filed on Apr. 21, 2017.

(51) Int. Cl.
| | | |
|---|---|---|
| *A61F 2/46* | (2006.01) | |
| *A61B 17/88* | (2006.01) | |
| *A61B 17/17* | (2006.01) | |
| *A61B 17/16* | (2006.01) | |

(52) U.S. Cl.
CPC ...... *A61B 17/8897* (2013.01); *A61B 17/1684* (2013.01); *A61B 17/1778* (2016.11)

(58) Field of Classification Search
CPC combination set(s) only.
See application file for complete search history.

(56) References Cited

U.S. PATENT DOCUMENTS

| | | |
|---|---|---|
| 6,045,581 A | 4/2000 | Burkinshaw |
| 6,398,815 B1 | 6/2002 | Pope |
| 6,676,705 B1 | 1/2004 | Wolf |
| 6,736,851 B2 | 5/2004 | Maroney et al. |
| 6,827,740 B1 | 12/2004 | Michelson |
| 6,887,277 B2 | 5/2005 | Rauscher et al. |

(Continued)

FOREIGN PATENT DOCUMENTS

| | | |
|---|---|---|
| CN | 1697633 | 11/2005 |
| CN | 102670334 | 9/2012 |

(Continued)

OTHER PUBLICATIONS

"Japanese Application Serial No. 2016-535678, Office Action dated Sep. 11, 2018", (W English Translation), 7 pgs.

(Continued)

*Primary Examiner* — Sameh R Boles
(74) *Attorney, Agent, or Firm* — Schwegman Lundberg & Woessner, P.A.

(57) ABSTRACT

A method for placing a first guide wire in a patient is disclosed. The method can include locating a model axis in a model and placing a second guide wire at the model axis, the model axis corresponding to an anatomical axis of an anatomical feature. The method can include coupling a guide plate to the second guide wire and the model. The method can include coupling an axis guide to the guide plate. The method can include decoupling the guide plate and the axis guide as an alignment unit from the second guide wire and coupling the guide plate and the axis guide as an alignment unit to the anatomical feature of the patient. The method can include using the alignment unit to place the first guide wire in the anatomical feature of the patient at the anatomical axis of the anatomical feature.

19 Claims, 9 Drawing Sheets

(56) References Cited

U.S. PATENT DOCUMENTS

| | | | |
|---|---|---|---|
| 6,986,790 | B2 | 1/2006 | Ball et al. |
| 7,097,663 | B1 | 8/2006 | Nicol et al. |
| 7,615,080 | B2 | 11/2009 | Ondrla |
| 7,819,923 | B2 | 10/2010 | Stone et al. |
| 8,002,838 | B2 | 8/2011 | Klotz |
| 8,052,758 | B1 | 11/2011 | Winslow |
| 8,192,497 | B2 | 6/2012 | Ondrla |
| 8,236,059 | B2 | 8/2012 | Stone et al. |
| 9,033,990 | B2 * | 5/2015 | Iannotti ............. A61B 17/1778 606/87 |
| 10,449,054 | B2 | 10/2019 | Hopkins |
| 2004/0064188 | A1 | 4/2004 | Ball et al. |
| 2004/0064190 | A1 | 4/2004 | Ball et al. |
| 2004/0230197 | A1 | 11/2004 | Tornier et al. |
| 2004/0267284 | A1 * | 12/2004 | Parmer ................. A61B 90/11 606/130 |
| 2007/0112430 | A1 | 5/2007 | Simmen et al. |
| 2009/0019262 | A1 | 1/2009 | Tashiro et al. |
| 2009/0125111 | A1 | 5/2009 | Copf, Jr. |
| 2009/0192621 | A1 | 7/2009 | Winslow et al. |
| 2011/0029088 | A1 | 2/2011 | Rauscher et al. |
| 2011/0106267 | A1 | 5/2011 | Grant |
| 2011/0196430 | A1 | 8/2011 | Walsh et al. |
| 2012/0046699 | A1 | 2/2012 | Jones et al. |
| 2015/0150687 | A1 | 6/2015 | Hopkins |
| 2018/0303551 | A1 | 10/2018 | Hopkins |
| 2020/0000600 | A1 | 1/2020 | Hopkins |

FOREIGN PATENT DOCUMENTS

| | | |
|---|---|---|
| CN | 1596091 | 3/2015 |
| CN | 105939682 | 9/2016 |
| DE | 10123517 | 11/2002 |
| DE | 102006002211 | 7/2007 |
| DE | 102006002211 | 9/2007 |
| EP | 0715836 | 6/1996 |
| EP | 0715836 | 10/2001 |
| EP | 1402856 | 3/2004 |
| FR | 2909860 A1 | 6/2008 |
| JP | 2004121849 | 4/2004 |
| JP | 2013521095 | 6/2013 |
| JP | 2013536022 | 9/2013 |
| JP | 2016538929 | 12/2016 |
| KR | 20130052542 | 5/2013 |
| WO | 0182843 | 11/2001 |
| WO | 2015084791 | 6/2015 |
| WO | 2016053837 | 4/2016 |

OTHER PUBLICATIONS

"European Application Serial No. 14821928.0, Response filed Oct. 8, 2018 to Communication Pursuant to Article 94(3) EPC dated Mar. 27, 2018", 12 pgs.

"Chinese Application Serial No. 201480072332.9, Office Action dated Sep. 30, 2018", (W English Translation), 16 pgs.

"Practical Manual of Basic Standards for Social Public Safety Product Design", Office of Technical Supervision Committee of Ministry of Public Security, Standards Press of China, not in English, (Dec. 31, 1995), 12 pgs.

U.S. Appl. No. 14/557,763, Response Filed Dec. 18, 2018 to Non-Final Office Action dated Sep. 18, 2018, 13 pgs.

"U.S. Appl. No. 14/557,763, Final Office Action dated Mar. 26, 2019", 11 pgs.

"U.S. Appl. No. 14/557,763, Notice of Allowability dated Aug. 14, 2019", 2 pgs.

"U.S. Appl. No. 14/557,763, Notice of Allowability dated Sep. 11, 2019", 3 pgs.

"U.S. Appl. No. 14/557,763, Notice of Allowance dated Jun. 10, 2019", 11 pgs.

"U.S. Appl. No. 14/557,763, Response filed May 22, 2019 to Final Office Action dated Mar. 26, 2019", 18 pgs.

"U.S. Appl. No. 15/956,502, Restriction Requirement dated Oct. 24, 2019", 7 pgs.

"U.S. Appl. No. 16/567,755, Preliminary Amendment filed Oct. 23, 2019", 7 pgs.

"Australian Application Serial No. 2014357337, Response filed Jul. 17, 2019 to Subsequent Examiners Report dated Dec. 19, 2018", 13 pgs.

"Canadian Application Serial No. 2,932,585, Office Action dated Jun. 14, 2019", 6 pgs.

"English abstract of FR 2909860", (2008).

"European Application Serial No. 18168424.2, Response filed Dec. 13, 2019 to Extended European Search Report dated Feb. 8, 2019", 16 pgs.

"European Application Serial No. 18168597.5, Extended European Search Report dated May 14, 2019", 10 pgs.

"U.S. Appl. No. 15/956,502, Response filed Dec. 13, 2019 to Restriction Requirement dated Oct. 24, 2019", 7 pages.

"Korean Application Serial No. 10-2016-7017889, Notice of Preliminary Rejection dated Dec. 19, 2019", 10 pages (5 pages official copy and 5 pages English translation).

"European Application Serial No. 18168597.5, Response filed Dec. 12, 2019 to Extended European Search Report dated May 14, 2019", with English claims, 16 pages.

"Canadian Application Serial No. 2,932,585, Response filed Dec. 16, 2019 to Office Action dated Jun. 14, 2019", 16 pages.

"U.S. Appl. No. 15/956,502, Non Final Office Action dated Jan. 10, 2020", 8 pages.

"European Application Serial No. 14821928.0, Communication Pursuant to Article 94(3) EPC dated Feb. 20, 2020", 4 pages.

"Korean Application Serial No. 10-2016-7017889, Response filed Feb. 26, 2020 Notice of Preliminary Rejection dated Dec. 19, 2019", with English claims, 8 pages.

"European Application Serial No. 18168597.5, Partial European Search Report dated Feb. 5, 2019", 10 pgs.

"European Application Serial No. 18168424.2, Extended European Search Report dated Feb. 8, 2019", 8 pgs.

"International Application Serial No. PCT US2014 068062, International Search Report dated Mar. 17, 2015", 4 pgs.

"International Application Serial No. PCT US2014 068062, Written Opinion dated Mar. 17, 2015", 6 pgs.

"International Application Serial No. PCT US2014 068062, International Preliminary Report on Patentability dated Jun. 16, 2016", 8 pgs.

"U.S. Appl. No. 14/557,763, Non Final Office Action dated Sep. 8, 2016", 12 pgs.

"U.S. Appl. No. 14/557,763, Response filed Nov. 18, 2016 to Non Final Office Action dated Sep. 8, 2016", 12 pgs.

"U.S. Appl. No. 14/557,763, Final Office Action dated Jan. 23, 2017", 13 pgs.

"European Application Serial No. 14821928.0, Response filed Dec. 16, 2016 to Communication pursuant to Rules 161(1) and 162 EPC dated Aug. 30, 2016", 12 pgs.

"U.S. Appl. No. 14/557,763, Response filed Mar. 3, 2017 to Final Office Action dated Jan. 23, 2017", 12 pgs.

"U.S. Appl. No. 14/557,763, Non Final Office Action dated Jun. 27, 2017", 12 pgs.

"U.S. Appl. No. 14/557,763, Response filed Sep. 27, 2017 to Non Final Office Action dated Jun. 27, 2017", 12 pgs.

"U.S. Appl. No. 14/557,763, Final Office Action dated Jan. 11, 2018", 11 pgs.

"Chinese Application Serial No. 201480072332.9, Office Action dated Jan. 24, 2018", (W English Translation), 16 pgs.

"European Application Serial No. 14821928.0, Communication Pursuant to Article 94(3) EPC dated Mar. 27, 2018", 5 pgs.

"U.S. Appl. No. 14/557,763, Response Filed Apr. 11, 2018 to Final Office Action dated Jan. 11, 2018", 17 pgs.

"Australian Application Serial No. 2014357337, First Examination Report dated Aug. 3, 2018", 5 pgs.

"U.S. Appl. No. 14/557,763, Non Final Office Action dated Sep. 18, 2018", 8 pgs.

"U.S. Appl. No. 15/956,502, Response filed Apr. 1, 2020 to Non Final Office Action dated Jan. 10, 2020", 12 pgs.

(56) References Cited

OTHER PUBLICATIONS

"Canadian Application Serial No. 2,932,585, Office Action dated Apr. 7, 2020", 3 pgs.
"Canadian Application Serial No. 2,932,585, Response filed May 12, 2020 to Office Action dated Apr. 7, 2020", 4 pgs.
"U.S. Appl. No. 15/956,502, Notice of Allowance dated Jul. 28, 2020", 9 pages.
"European Application Serial No. 14821928.0, Response filed Jul. 1, 2020 to Communication Pursuant to Article 94(3) EPC dated Feb. 20, 2020", 28 pages.

* cited by examiner

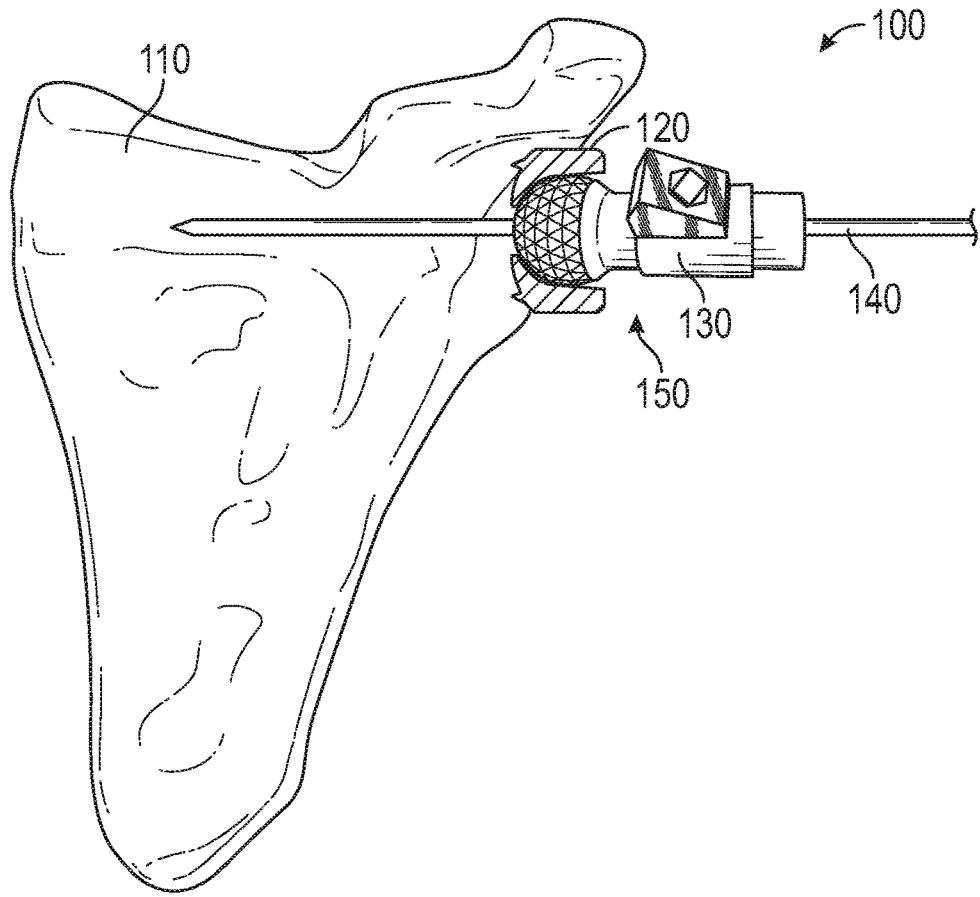
FIG. 1
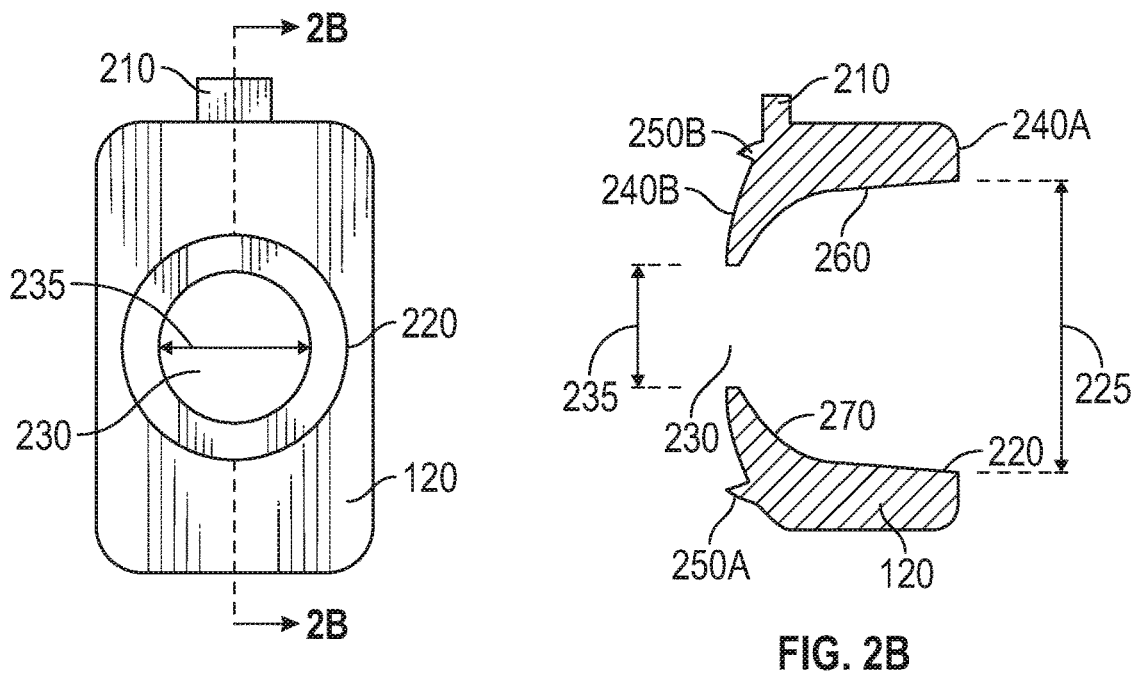
FIG. 2A
FIG. 2B

GUIDE WIRE ALIGNMENT

CLAIM OF PRIORITY

This application claims the benefit of U.S. Provisional Patent Application Ser. No. 62/488,472, filed on Apr. 21, 2017, the benefit of priority of which is claimed hereby, and which is incorporated by reference herein in its entirety.

BACKGROUND

One or more conditions (e.g., injury, bone spurs, arthritis, developmental disorder, or the like) can affect a joint (e.g., a shoulder or hip joint) and necessitate a medical procedure (e.g., total shoulder arthroplasty) to correct the one or more conditions. In an example, a surgeon conducting a total shoulder arthroplasty on a patient can place guide wires in the patient's anatomy to guide the surgeon in conducting the medical procedure.

SUMMARY

A problem to be solved can include the mal-alignment of replacement anatomy (e.g., a prosthetic device) during a medical procedure to install the replacement anatomy. Mal-alignment of replacement anatomy can be caused by a variety of factors (e.g., poor visibility of the anatomy undergoing the medical procedure, limited access to the anatomy, guesswork by a surgeon, or the like). In an example, a lack of ability to observe the anatomy undergoing a medical procedure can result in a mal-alignment of the replacement anatomy. Observation of the anatomy of the joint during the medical procedure can be hampered by the one or more conditions or by limited access to the joint itself (e.g., other anatomical features are blocking physical access to, or visual inspection of, the anatomy under observation). The mal-alignment of the replacement anatomy can have negative effects upon the efficacy of the medical procedure. Additionally, instruments can be fabricated that are specific to the patient's anatomy. The patient-specific instruments can allow for an individual (e.g., a radiologist, a surgeon, a nurse, or the like) to facilitate accurate alignment of the replacement anatomy. However, patient-specific instrument fabrication can be expensive, can require specialized equipment, such as computerized tomography scanners, or can take considerable time to fabricate the model. Further, because the instrument is patient-specific, the instrument cannot be re-used in a different medical procedure.

In an example wherein a patient is undergoing a total shoulder arthroplasty procedure, the diminished ability to observe the anatomy of the shoulder joint can result in the mal-alignment, or improper installation, of replacement anatomy (e.g., a shoulder joint replacement apparatus). The mal-alignment of the replacement anatomy can negatively affect the durability or performance of the replacement anatomy. In an example, the mal-alignment of the replacement anatomy can cause a premature loosening of the replacement anatomy from the patient's anatomy or cause pain to the patient. A decrease in the durability or performance of the replacement anatomy can necessitate further medical procedures, or otherwise negatively affect the quality of life of the patient.

A solution to the aforementioned problems to be solved can include a method for placing a first guide wire in a patient. The method can include locating a model axis in a model, the model axis corresponding to an anatomical axis of an anatomical feature. The method can include placing a second guide wire in the model located at the model axis. The method can include coupling a guide plate to the second guide wire and the model, wherein the guide plate can include a first guide wire bore. The method can include coupling an axis guide to the guide plate, wherein coupling the axis guide can include translating the second guide wire through a second guide wire bore of the axis guide. The method can include decoupling the guide plate and the axis guide as an alignment unit from the second guide wire. The method can include coupling the guide plate and the axis guide as an alignment unit to the anatomical feature of the patient. The method can include placing the first guide wire in the anatomical feature of the patient, wherein the coupling of the axis guide with the guide plate allows the first guide wire to be located at the anatomical axis of the anatomical feature.

In an example, the alignment unit can be used to couple a first guide wire with the anatomical feature. In an example, the anatomical feature can be a scapula or a hip bone. The alignment unit can be used to locate the first guide wire at the anatomical axis of the anatomical feature. The alignment unit can assist in accurately and precisely placing the first guide wire at the anatomical axis of the anatomical feature. The alignment unit can allow for an individual (e.g., a surgeon, nurse, or the like) to establish the relative angles of the axis guide to the guide plate with the model outside of a patient. Establishing the relative angles with the model can simplify installation of a replacement anatomy (e.g., a femoral head or a humeral head) by simplifying the identification of a mounting location (e.g., the anatomical axis) for the replacement anatomy. Establishing the relative angles with the model can simplify installation of the replacement anatomy by eliminating obstructions (e.g., other anatomical features) while identifying the mounting location for the replacement anatomy.

Aspect 1 can include or use subject matter (such as an apparatus, a system, a device, a method, a means for performing acts, or a device readable medium including instructions that, when performed by the device, can cause the device to perform acts), such as can include or use a method for placing a first guide wire in a patient. The method can include locating a model axis in a model, the model axis corresponding to an anatomical axis of an anatomical feature of the patient. The method can include placing a second guide wire in the model located at the model axis. The method can include coupling a guide plate to the second guide wire and the model, wherein the guide plate includes a first guide wire bore. The method can include coupling an axis guide to the guide plate, wherein coupling the axis guide includes translating the second guide wire through a second guide wire bore of the axis guide. The method can include decoupling the guide plate and the axis guide as an alignment unit from the second guide wire. The method can include coupling the guide plate and the axis guide as an alignment unit to the anatomical feature of the patient. The method can include placing the first guide wire in the anatomical feature of the patient, wherein the coupling of the axis guide with the guide plate allows the first guide wire to be located at the anatomical axis of the anatomical feature.

Aspect 2 can include or use, or can optionally be combined with the subject matter of Aspect 1, to optionally include or use decoupling the guide plate and the axis guide from the anatomical feature.

Aspect 3 can include or use, or can optionally be combined with the subject matter of one or any combination of Aspects 1 or 2 to optionally include or use that the anatomical feature is a glenoid or an acetabulum.

Aspect 4 can include or use, or can optionally be combined with the subject matter of one or any combination of Aspects 1 through 3 to optionally include or use identifying an anatomical geometry of an anatomical feature of the patient, wherein the geometry of the anatomical feature includes an anatomical axis.

Aspect 5 can include or use, or can optionally be combined with the subject matter of one or any combination of Aspects 1 through 4 to optionally include or use fabricating the model of the anatomical feature including a model geometry, the model geometry corresponding to the anatomical geometry of the anatomical feature of the patient.

Aspect 6 can include or use, or can optionally be combined with the subject matter of one or any combination of Aspects 1 through 5 to optionally include or use that fabricating the model includes fabricating the model by a process including machining, stereolithography, digital light processing, fused deposition modeling, selective laser sintering, selective laser melting, electronic beam melting, or laminated object manufacturing.

Aspect 7 can include or use, or can optionally be combined with the subject matter of one or any combination of Aspects 1 through 6 to optionally include or use that identifying the anatomical geometry of the anatomical feature includes determining the anatomical geometry by performing medical imaging of the anatomical feature, the medical imaging including x-ray, magnetic resonance imaging, computed tomography scan, or ultrasound.

Aspect 8 can include or use, or can optionally be combined with the subject matter of one or any combination of Aspects 1 through 7 to optionally include or use that placing the first guide wire or the second guide wire includes mechanically fastening the first guide wire or the second guide wire to the anatomical feature or the model, respectively.

Aspect 9 can include or use, or can optionally be combined with the subject matter of one or any combination of Aspects 1 through 8 to optionally include or use marking a first indicator on the model at a first location and marking a second indicator on the anatomical feature at a second location, wherein the first location corresponds with the second location.

Aspect 10 can include or use, or can optionally be combined with the subject matter of one or any combination of Aspects 1 through 9 to optionally include or use aligning one or more alignment indicia of the guide plate with the first indicator.

Aspect 11 can include or use, or can optionally be combined with the subject matter of one or any combination of Aspects 1 through 10 to optionally include or use aligning one or more alignment indicia of the guide plate with the second indicator.

Aspect 12 can include or use, or can optionally be combined with the subject matter of one or any combination of Aspects 1 through 11 to optionally include or use that placing the first guide wire includes translating the first guide wire through the second guide wire bore in the axis guide and the first guide wire bore in the guide plate.

Aspect 13 can include or use, or can optionally be combined with the subject matter of one or any combination of Aspects 1 through 12 to optionally include or use that a diameter of the first guide wire bore is greater than a diameter of the second guide wire bore.

Aspect 14 can include or use, or can optionally be combined with the subject matter of one or any combination of Aspects 1 through 13 to optionally include or use that the first guide wire bore is configured to allow the first or second guide wire to translate through the guide plate in one or more orientations.

Aspect 15 can include or use, or can optionally be combined with the subject matter of one or any combination of Aspects 1 through 14 to optionally include or use that the second guide wire bore is configured to allow the first or second guide wire to translate through the axis guide in a single orientation.

Aspect 16 can include or use, or can optionally be combined with the subject matter of one or any combination of Aspects 1 through 15 to optionally include or use that the axis guide is configured to couple with the guide plate at one or more orientations.

Aspect 17 can include or use, or can optionally be combined with the subject matter of one or any combination of Aspects 1 through 16 to optionally include or use that the patient is a first patient. The method can include sanitizing the guide plate and axis guide. The method can include coupling the guide plate and axis guide to an anatomical feature of a second patient.

Aspect 18 can include or use subject matter (such as an apparatus, a system, a device, a method, a means for performing acts, or a device readable medium including instructions that, when performed by the device, can cause the device to perform acts), such as can include or use a guide wire placement apparatus. The apparatus can include a guide plate. The guide plate can include a first guide plate surface configured to couple with an anatomical feature of a patient. The guide plate can include a second guide plate surface opposite the first guide plate surface. The guide plate can include a guide plate socket extending into the first guide plate surface. The guide plate can include a guide wire bore extending from the socket to the second guide plate surface to allow a guide wire to translate through the guide plate. The apparatus can include an axis guide. The axis guide can include a coupling member configured to lock into the socket in multiple positions. The axis guide can include a second guide wire bore passing through the axis guide. The second guide wire bore can be configured to allow the guide wire to translate through the second guide wire bore in one position. The positionable mating of the coupling member with the guide plate bore can align the first guide wire bore with the second guide wire bore.

Aspect 19 can include or use, or can optionally be combined with the subject matter of Aspect 18, to optionally include or use that the anatomical feature is a scapula or a hip bone.

Aspect 20 can include or use, or can optionally be combined with the subject matter of one or any combination of Aspects 18 or 19 to optionally include or use that the guide plate includes an indicator, wherein the indicator is configured to be aligned with a portion of the anatomical feature.

Aspect 21 can include or use, or can optionally be combined with the subject matter of one or any combination of Aspects 18 through 20 to optionally include or use that the axis guide includes a mounting location, the mounting location used to couple with a handle.

Aspect 22 can include or use, or can optionally be combined with the subject matter of one or any combination of Aspects 18 through 21 to optionally include or use the guide plate socket is tapered.

Aspect 23 can include or use, or can optionally be combined with the subject matter of one or any combination of Aspects 18 through 22 to optionally include or use that the first guide plate surface includes one or more surface features that are configured to increase the friction coefficient of the first guide plate surface.

Aspect 24 can include or use, or can optionally be combined with the subject matter of one or any combination of Aspects 18 through 23 to optionally include or use that the coupling member is quasi-spherical, and the one or more surface features are in communication with a surface of the guide plate socket.

Aspect 25 can include or use subject matter (such as an apparatus, a system, a device, a method, a means for performing acts, or a device readable medium including instructions that, when performed by the device, can cause the device to perform acts), such as can include or use a system for placing a first guide wire in a patient. The system can include a model including a model axis, wherein the model axis corresponds to an anatomical axis of an anatomical feature. The system can include a second guide wire coupled with the model at the model axis. The system can include a guide plate. The guide plate can include a first guide plate surface configured to couple with an anatomical feature of a patient. The guide plate can include a second guide plate surface opposite the first guide plate surface. The guide plate can include a guide plate socket extending into the first guide plate surface. The guide plate can include a guide wire bore extending from the socket to the second guide plate surface to allow a guide wire to translate through the guide plate. The system can include an axis guide. The axis guide can include a coupling member configured to lock into the socket in multiple positions. The axis guide can include a second guide wire bore passing through the axis guide, wherein the second guide wire bore is configured to allow the guide wire to translate through the second guide wire bore in one position. The positionable mating of the coupling member with the guide plate bore can align the first guide wire bore with the second guide wire bore.

Aspect 26 can include or use, or can optionally be combined with the subject matter of Aspect 25, to optionally include or use that the coupling member is quasi-spherical, and the one or more surface features are in communication with the walls of the guide plate socket.

Aspect 27 can include or use, or can optionally be combined with the subject matter of one or any combination of Aspects 25 or 26 to optionally include or use that the guide plate socket is tapered.

Aspect 28 can include or use, or can optionally be combined with the subject matter of one or any combination of Aspects 25 through 27 to optionally include or use an alignment rig, wherein the alignment rig is configured to couple with the model and locate the model axis.

Aspect 29 can include or use, or can optionally be combined with the subject matter of one or any combination of Aspects 25 through 28 to optionally include or use the model is an anatomy simulator configured for setting the relative angles.

Aspect 30 can include or use subject matter (such as an apparatus, a system, a device, a method, a means for performing acts, or a device readable medium including instructions that, when performed by the device, can cause the device to perform acts), such as can include or use a method for calibrating adjustable orthopaedic devices. The method can include identifying an anatomical geometry of an anatomical feature of the patient, wherein the geometry of the anatomical feature includes an anatomical axis. The method can include coupling a first guide wire to an anatomy simulator, wherein the anatomy simulator is configured to reproduce the anatomical axis. The method can include coupling a guide plate with the anatomy simulator, wherein coupling the guide plate with the anatomy simulator includes translating the first guide wire through a first guide wire bore of the guide plate, the first guide wire bore configured to allow first guide wire to translate through the guide plate in one or more orientations. The method can include coupling an axis guide to the guide plate, wherein coupling the axis guide includes translating the first guide wire through a second guide wire bore of the axis guide, the second guide wire bore configured to receive the first guide wire in a single orientation. The method can include decoupling the guide plate and the axis guide as a unit from the first guide wire. The method can include coupling the guide plate and the axis guide as a unit to the anatomical feature of the patient. The method can include placing a second guide wire in the anatomical feature of the patient, wherein the coupling of the axis guide with the guide plate allows the second guide wire to be located at the anatomical axis of the anatomical feature.

Aspect 31 can include or use, or can optionally be combined with the subject matter of Aspect 30, to optionally include or use that the anatomy simulator includes one or more faces, wherein the faces include a simulator socket.

Aspect 32 can include or use, or can optionally be combined with the subject matter of one or any combination of Aspects 30 or 31 to optionally include or use that the anatomy simulator is a reproduction of the anatomical feature.

Aspect 33 can include or use subject matter (such as an apparatus, a system, a device, a method, a means for performing acts, or a device readable medium including instructions that, when performed by the device, can cause the device to perform acts), such as can include or use an anatomy simulator. The anatomy simulator can include a guide body having one or more faces. The anatomy simulator can include a first simulator socket forming a recess in a first face of the one or more faces. The first simulator socket can be configured to receive a guide plate. The first simulator socket can includes a base portion. A guide wire bore can extend from the base portion of the first simulator socket to the interior of the anatomy simulator. The guide wire bore can be configured to receive a guide wire in a single orientation.

Aspect 34 can include or use, or can optionally be combined with the subject matter of Aspect 33, to optionally include or use the first base portion is angled at a first angle with respect to the first face.

Aspect 35 can include or use, or can optionally be combined with the subject matter of one or any combination of Aspects 33 or 34 to optionally include or use simulator indicia on the first face configured to provide alphanumerical information identifying the first angle.

Aspect 36 can include or use, or can optionally be combined with the subject matter of one or any combination of Aspects 33 through 35 to optionally include or use that the first socket includes one or more indicator portions configured to receive an alignment indicia of a guide plate.

Aspect 37 can include or use, or can optionally be combined with the subject matter of one or any combination of Aspects 33 through 36 to optionally include or use that the first face includes a first simulator indicia configured to provide alphanumerical information identifying the first angle. The first simulator socket can include a first indicator portion configured to receive an alignment indicia of the guide plate. Aligning the alignment indicia with the first indicator portion and mating the guide plate with the anatomy simulator can impart the first angle onto the guide plate with respect to the first face.

Aspect 38 can include or use, or can optionally be combined with the subject matter of one or any combination of Aspects 33 through 37 to optionally include or use that the guide wire bore is configured to extend orthogonally to the first face.

Aspect 39 can include or use, or can optionally be combined with the subject matter of one or any combination of Aspects 33 through 38 to optionally include or use that the first simulator socket is included in a plurality of simulator sockets and each of the one or more faces includes an individual simulator socket of the plurality of sockets.

Aspect 40 can include or use, or can optionally be combined with the subject matter of one or any combination of Aspects 33 through 39 to optionally include or use the guide plate. The guide plate can include a first guide plate surface configured to couple with an anatomical feature of a patient. The guide plate can include a second guide plate surface opposite the first guide plate surface. The guide plate can include a guide plate socket extending into the first guide plate surface. The guide plate can include a guide wire bore extending from the socket to the second guide plate surface to allow a guide wire to translate through the guide plate.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a posterior view of an example of a guide wire alignment system.

FIG. 2A is front view of an example of a guide plate for placing a first guide wire.

FIG. 2B is a cross-sectional view of the guide plate of FIG. 1 at the sectional line 2B-2B.

DETAILED DESCRIPTION

Figure 3:
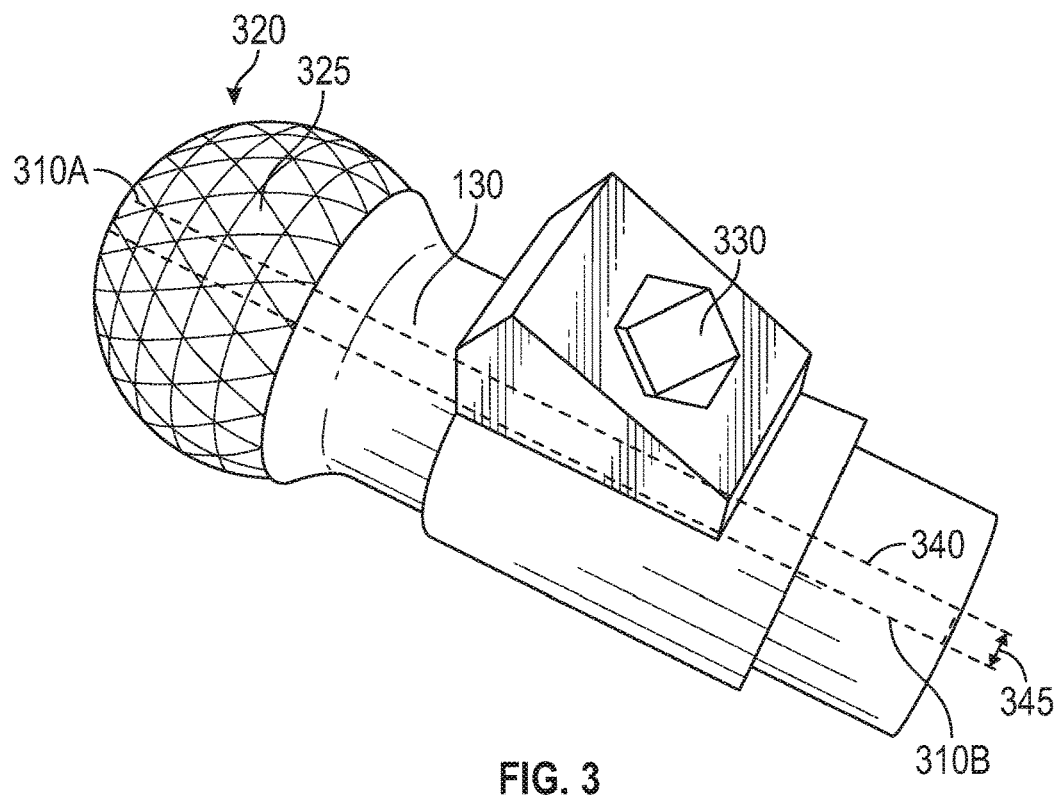
FIG. 3 is a perspective view of an example of an axis guide for placing a first guide wire.

FIG. 1 is a posterior view of an example of a guide wire alignment system 100. The guide wire alignment system 100 can include an anatomical feature 110, a guide plate 120, an axis guide 130, and a first guide wire 140. The guide plate 120 and the axis guide 130 can be mated together. The mated assembly of the guide plate 120 and the axis guide 130 can be referred to as an alignment unit 150. The alignment unit 150 can be configured to allow the fixable positioning of the axis guide 130 with respect to the guide plate 130. The first guide wire 140 can translate through the axis guide 130 and the guide plate 120. The alignment unit 150 can be used to place the first guide wire 140 in the anatomical feature 110 at a specific location and/or at a specific orientation.

FIG. 2A is front view of an example of a guide plate 120 for placing a first guide wire. In an example, the guide plate 120 can include alignment indicia 210, a socket 220, a first guide wire bore 230, and a first diameter 235. In an example, the alignment indicia 210 can be used to align the guide plate 120 with a landmark or indicator (e.g., a marking on the anatomical feature 110 of FIG. 1 or a model of the anatomical feature 110). The alignment indicia 210 can be a feature (e.g., a protrusion) extending from the guide plate 110. The alignment indicia 210 can be a marking (e.g., recess, slot, groove, depression, indent, deboss, emboss, raised dot, raised line, or the like) on a surface of the guide plate 120. In an example, the first guide wire bore 230 can have a first diameter 235. In an example, first guide wire bore 230 can be configured to allow a guide wire to translate through the guide plate 120 in one or more orientations. The first diameter 235 can be greater than, or equal to, a diameter of a guide wire (e.g., the first guide wire 140 of FIG. 1). In an example, the socket 230 can be configured to receive an axis guide (e.g., the axis guide 130 of FIG. 1). The socket 230 can be configured to mate with, or otherwise couple with, the axis guide. The socket 230 can mate with the axis guide through the interaction of surface features on the axis guide with the socket 230.

FIG. 2B is a cross-sectional view of the guide plate 120 of FIG. 1 at the sectional line 2B-2B. In an example, the guide plate 120 can include the alignment indicia 210, the socket 220, a second diameter 225, the first guide wire bore 230, the first diameter 235, a first surface 240A, a second surface 240B, one or more guide plate surface features 250A and 250B, and a tapered surface 260. The guide plate 120 can include one or more alignment indicia 210.

In an example, the one or more guide plate surface features 250A and 250B can extend from the second surface 240B. The one or more guide plate surface features 250A and 250B can be coupled to, and extend from, the second surface 240B. The one or more guide plate surface features 250A and 250B can extend from the first surface 240A. The one or more guide plate surface features 250A and 250B can be protrusions (e.g., spikes, teeth, or the like) that extend from either the first surface 240A or the second surface 240B. The one or more guide plate surface features 250A and 250B can extend from the first surface 240A. The guide plate 120 can include one or more guide plate surface features 250A and 250B over the entire second surface 240B. The one or more guide plate surface features 250A and 250B can increase the coefficient of friction of the second surface 240B by introducing roughness to the second surface 240B. The one or more guide plate surface features 250A and 250B can allow for the guide plate 120 to remain in the orientation desired, such as the orientation desired by a surgeon.

In an example, the first guide wire bore 230 has a first diameter 235. In an example, the first guide wire bore 230 can extend from the second surface 240B and open into the socket 230. The socket 230 can have a second diameter 165. The second diameter can be greater than a diameter of a head of an axis guide. In an example, the socket 230 can be configured to mate with, or otherwise couple with, an axis guide (e.g., axis guide 130 of FIG. 1). The socket 230 can mate with the axis guide through the interaction of surface features on the head of the axis guide with the socket 230.

The socket 230 can have a tapered surface 260. The tapered surface 260 can increase the surface area in contact with the axis guide and thereby increase the friction between the socket 230 and the axis guide. The tapered surface 260 can include guide plate surface features that correspond with the surface features on the head of the axis guide. The tapered surface 260 can become gradually smaller in diameter from the first surface 240A toward first guide wire bore 230. The tapered surface 260 can be configured to ease the insertion of the axis guide 130 into the socket 220. The tapered surface 260 can ease the insertion of the axis guide 130 by providing an opening that has a greater dimension than the axis guide 130. In an example, the second diameter 225 can be greater than the diameter of a head of the axis guide 130. The tapered surface 260 can allow an individual to readily place the axis guide 130 within the socket 220 and then drive the axis guide 130 into the socket, thereby mating the axis guide 130 with the socket 220.

Additionally, the tapered surface 260 can merge into a contoured portion 270. The contoured portion 270 can have a radius of curvature that can mate with the radius of curvature of a guide axis. In an example, the contoured portion 270 can have a first radius of curvature that is configured to mate with a second radius of curvature of a head of the axis guide 130. The first radius of curvature can be the same as the second radius of curvature. The contoured portion can merge into the first guide wire bore 230.

FIG. 3 is a perspective view of an example of an axis guide 130 for placing a first guide wire (e.g., the first guide wire 140 of FIG. 1). In an example, the axis guide 130 can include a first end 310A, a second end 310B, a head 320, surface features 325, a mounting location 330, and a second guide wire bore 340. In an example, the second guide wire bore 340 can be configured to extend from a first end 310A of the axis guide 130 to a second end 310B of the axis guide 130. The second guide wire bore 340 can be configured to extend from the first end 310A of the axis guide 130 and partially toward the second end 310B of the axis guide 130. The second guide wire bore 340 can be located along a longitudinal axis of the axis guide 130. Stated another way the second guide wire bore 340 can be located in the center of the axis guide 130 and extend between the first and second ends 310A and 310B. In particular, in some embodiments, the head 320 can have a generally spherical shape defined by surface features 325 and the second guide wire bore 340 can pass through the geometric center of the spherical shape. The head 320 can have a second radius of curvature. The second radius of curvature can be the same as the first radius of curvature of the contoured portion 270 The second guide wire bore 340 can have dimensions less than, or equal to, a first guide wire bore (e.g., the first guide wire bore 230 of FIGS. 2A and 2B). The second guide wire bore 340 can have a third diameter 345. The third diameter 345 can be less than a first diameter of a guide plate (e.g., first diameter 235 of guide plate 120 of FIGS. 2A and 2B). In an example, the second guide wire bore 340 can be configured to receive a guide wire (e.g., the first guide wire 140 of FIG. 1). In an example, the second guide wire bore 340 can be configured to allow a guide wire to translate through the second guide wire bore 340.

In an example, the second guide wire bore 340 can be configured to allow a guide wire to translate through the axis guide 130 in a single orientation. Stated another way, the second guide wire bore 340 can be configured to allow a guide wire to translate through the axis guide without allowing a substantial amount of play in the movement of the guide wire within the second guide wire bore 340. The third diameter can be substantially the same diameter as (e.g., slightly larger than) a guide wire, such that the guide wire can be able to freely translate within the second guide wire bore 340, yet remain substantially parallel (e.g., within 10 degrees) to the longitudinal axis of the axis guide 130.

The amount of freedom, or play, allowed within the axis guide 130, with respect to a guide wire, differs from the amount of freedom allowed in a guide plate (e.g., the guide plate 120 of FIG. 1). As previously stated, a first guide wire bore (e.g., the first guide wire bore 230 of FIGS. 2A and 2B) can be configured to allow a guide wire to translate through a guide plate in one or more orientations. In an example, a guide wire can translate through a first guide wire bore at a variety of orientations (e.g., angles), such as because a first diameter of the guide wire bore can be substantially larger (e.g., 110% or more) than a diameter of the guide wire. This is in contrast to the guide wire only being able to translate through an axis guide (e.g., axis guide 130) in one orientation. The translation of the guide wire through the guide plate at an angle when the guide plate is attached to an anatomical feature can require that the axis guide 130 mate with the guide plate 120 at that angle, or substantially close to that angle (e.g., within 10 degrees). Stated another way, the second guide wire bore 340 can be configured to slide over a guide wire, but not allow angular misalignment between a longitudinal axis of the guide wire and a longitudinal axis of the second guide wire bore 340. In an example, the mounting location 340 can be configured to couple to a handle. The handle can be used to support (e.g., hold) the axis guide 130.

In an example, the axis guide 130 can include the head 320. The head 320 can be referred to as a coupling member. The head 320 can be quasi-spherical (e.g., substantially a sphere). In an example, an exterior surface of the head 320 can be configured to mate with a socket (e.g., the socket 230 of FIGS. 2A and 2B) of a guide plate (e.g., the guide plate 110 of FIGS. 2A and 2B). In an example, the exterior surface of the head 320 can be smooth. In another example, the exterior surface of the head 320 can include surface features 325. The surface features 325 can be facets on the surface of the head 320. The surface features 325 can be a plurality of triangular planar surfaces on the head 320. The surface features 325 can be a plurality of polygon-shaped (e.g., square, pentagon, octagon, or the like) planar surfaces on the head 320.

In an example, the mating of the head 320 of the axis guide 130 with the socket can allow for a fixable positioning of the axis guide 130 relative to the guide plate. Fixable positioning can also be referred to as positionable mating. Fixable positioning of the axis guide 130 can include when the position, or orientation, of the axis guide 130 relative to the guide plate remains fixed, or unchanged, once the position or orientation has been established or set, such as by a surgeon. Fixable positioning can be achieved by an interference fit between the head 320 and the socket. Fixable positioning can be achieved by an interaction of, or communication between, the surface features 325 with a surface of the socket. Fixable positioning can be achieved by an interaction of the surface features 325 with a tapered surface (e.g., tapered surface 260 of FIG. 2B) of the socket. The fixable positioning of the axis guide 130 can be achieved by fastening the axis guide 130 to the guide plate, thereby locking the axis guide 130 into a position relative to the guide plate.

In an example, the guide plate (e.g., the guide plate 120 of FIG. 1) can include a threaded hole that extends from the exterior of the guide plate into the socket. A fastener (e.g., a screw, bolt, or other threaded fastener) can be threaded through the hole and engage with the head 320, thereby fixing the position of the axis guide 130 relative to the guide plate. In another example, the guide plate can include a through hole that extends from the exterior of the guide plate into the socket. The axis guide 130 can include a plurality of corresponding holes that align with the through hole in the guide plate. A pin can be inserted into the through hole and the corresponding holes in the axis guide 130, thereby fixing the position of the axis guide 130 relative to the guide plate.

In an example, the quasi-spherical shape of head 320 can include surface features 325 that are similar to the faceted surfaces described in U.S. patent application Ser. No. 14/557,763 entitled "Adjustable Orthopedic Connections," filed on Dec. 2, 2014, which is hereby incorporated by reference herein in its entirety.

Figure 4A:
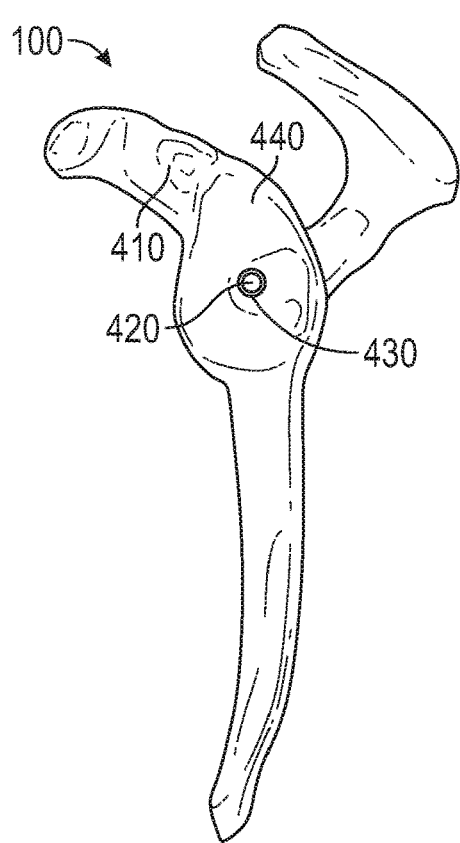
FIG. 4A is a lateral view of an example of a guide wire alignment system including a model of a scapula including a second guide wire.

FIG. 4A is a lateral view of an example of a guide wire alignment system 100 including a model 410 of a scapula including a second guide wire 430. In an example, an anatomical geometry of the anatomical feature can be identified, such as by a medical practitioner (e.g., a radiologist, nurse, surgeon, or the like). The anatomical geometry can include an anatomical axis. Identifying the anatomical geometry of the anatomical feature can include determining the anatomical geometry by performing medical imaging of the anatomical feature. Medical imaging techniques can include x-ray, magnetic resonance imaging, computed tomography scan, or ultrasound. The model 410 can be fabricated by a process including machining, stereolithography, digital light processing, fused deposition modeling, selective laser sintering, selective laser melting, electronic beam melting, or laminated object manufacturing.

In an example, the model 410 can be a replica or representation of an anatomical feature (e.g., the anatomical feature 110 of FIG. 1) of a patient. In an example, the model 410 can include a model geometry representative of the anatomical feature, the model geometry corresponding to the anatomical geometry of the anatomical feature of the patient. In an example, the anatomical feature can be a hip bone. In another example, the anatomical feature can be a scapula. In an example, the model 410 can be a replica or representation of the hip bone. In another example, the model 410 can be a replica or representation of the scapula. The model 410 of the scapula can include a glenoid cavity 440. The model 410 can include a model axis 420 that corresponds to an anatomical axis of the anatomical feature the model 410 replicates or represents. The second guide wire 430 can be located at the model axis 420 of the model 410. FIG. 4A is a view of the model 410 of the scapula that is perpendicular to the glenoid cavity 440. The second guide wire 430 can be located at the geometric center of the glenoid cavity 440. The second guide wire 430 can be located substantially at the geometric center of the glenoid cavity 440.

Figure 4B:
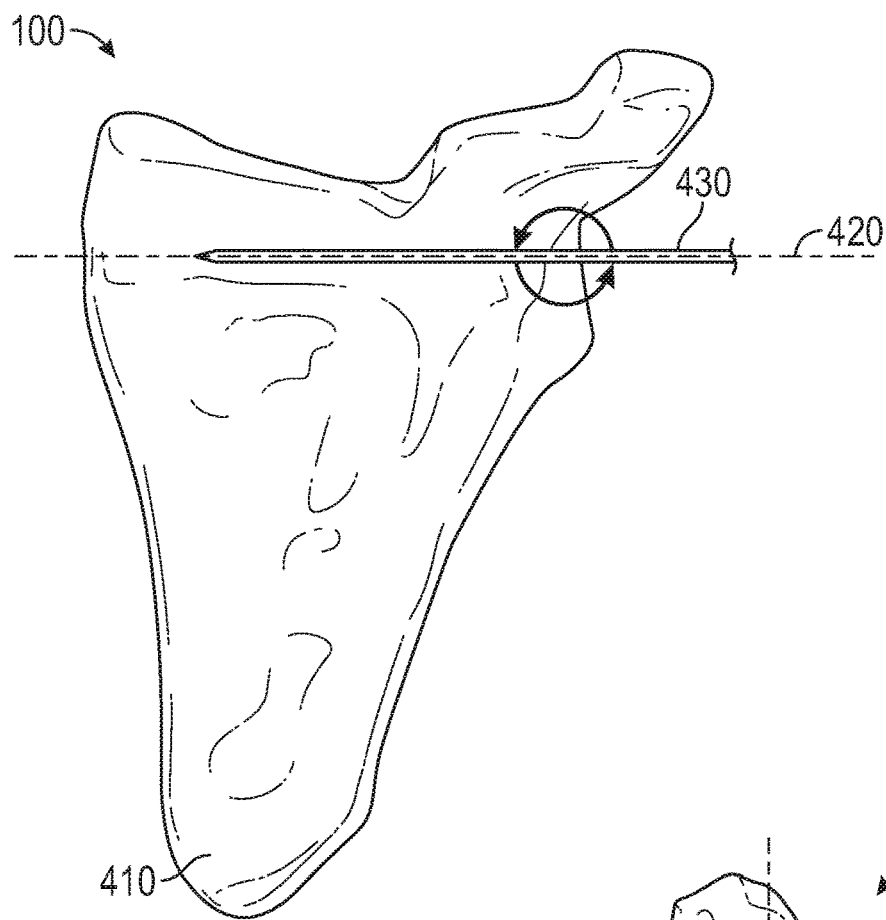
FIG. 4B is a posterior view of the guide wire alignment system including the model of the scapula of FIG. 4A showing a transverse axis through a glenoid.

FIG. 4B is a posterior view of the guide wire alignment system 100 including the model 410 of the scapula of FIG. 4A showing a transverse axis through a glenoid. In an example, a scapula can be an amorphous shaped anatomical feature. The amorphous shape of the scapula can present challenges in locating a guide wire within the scapula. For instance, thickness of the scapula can vary over its amorphous shape. Locating a region of the scapula that has a consistent thickness can be difficult due to the variations in the thickness of the scapula. In an example, the second guide wire 430 can be a fastener that couples with the scapula. The second guide wire 430 can be drilled, screwed, or otherwise implanted within the scapula. The second guide wire 430 requires sufficient structural support in order to perform as designed (e.g., remain coupled with the patient's anatomy). If the second guide wire 430 is not located in an area with sufficient structural support, the second guide wire could damage the anatomical feature coupled with the second guide wire 430, or the second guide wire 430 could loosen over time.

In an example, the model 410 can include a model axis 420. The model axis 420 can be located in a region of the model 410 that provides sufficient structural support for the coupling of a guide wire (e.g., the second guide wire 430). The model axis 420 can be located at the geometric center of a glenoid cavity or an acetabulum. In an example, an individual can locate the model axis 420 in the model 410 before placing the second guide wire 430. In an example, placing the second guide wire 430 at a location other than the model axis 420 (that corresponds to an anatomical axis of an anatomical feature) can reduce the efficacy of replacement anatomy. In an example, the second guide wire 430 can be used in a total shoulder arthroplasty that replaces portions of a patient's shoulder anatomy with a medical implant. If the second guide wire 430 is not located at the model axis 420, the efficacy of the medical implant can be diminished, such as by limiting the patient's range of motion, causing pain or discomfort within the patient, or necessitating further surgical procedures to replace the medical implant or otherwise modify the medical implant.

Figure 4C:
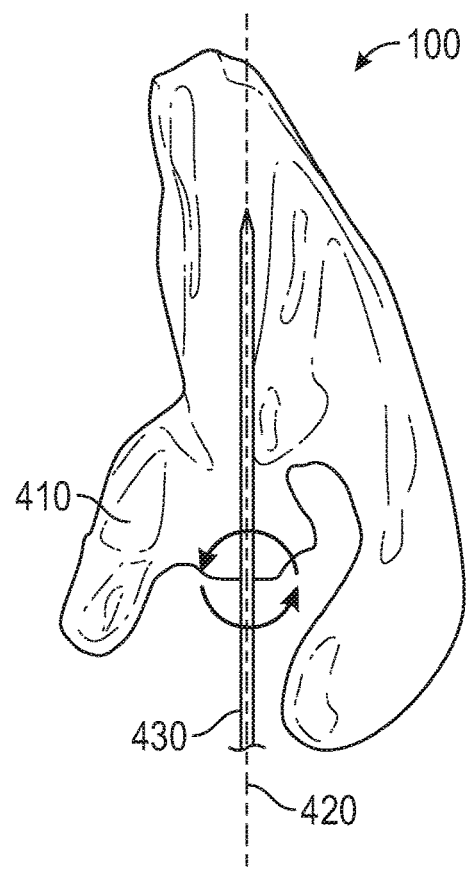
FIG. 4C is a superior view of the guide wire alignment system including the model of the scapula of FIG. 4A showing a coronal axis through the glenoid.

FIG. 4C is a superior view of the guide wire alignment system 100 including the model 410 of the scapula of FIG. 4A showing a coronal axis through the glenoid. In an example, the second guide wire 430 can include a longitudinal axis. In an example, the longitudinal axis of the second guide wire 430 can be collinear with the model axis 420. The collinearity of the longitudinal axis of the second guide wire 430 and the model axis 420 can ensure that the second guide wire 430 is located in a region with sufficient structural support to allow the second guide wire 430 to perform as designed. The collinearity of the longitudinal axis of the second guide wire 430 and the model axis 420 can improve the efficacy of a medical implant by ensuring that the medical implant is installed correctly within a patient.

An individual (e.g., a surgeon, radiologist, nurse, or the like) can evaluate the model 410 to determine how to place the second guide wire 430 in the model. An individual can evaluate the medical imaging to determine how to place the second guide wire 430 in the model. An individual can place the second guide wire 430 into the model 410 before a medical procedure is to be conducted on a patient. The second guide wire 430 can be placed into the model 410 for the purpose of assembling the guide plate 120 and the axis guide 130. Placing the second guide wire 430 in the model 410 can allow for an individual to use the model 410 to determine the correct position and orientation of the second guide wire 430 with respect to the model 410 outside of a patient. Use of the model 410 allows for a patient-specific determination of proper placement of the second guide wire 430. Use of the alignment unit 150 of FIG. 1 can allow for the position and orientation of the second guide wire 430 to be transferred, such that the first guide wire 140 can be placed in substantially (e.g., within 5 degrees of each axis) the same position and orientation within the anatomical feature 110, as the second guide wire 430 was placed in the model 410.

Figure 5A:
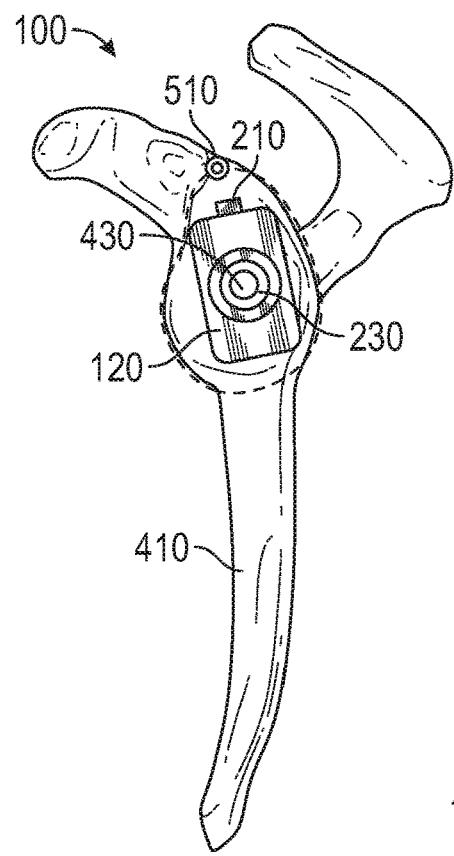
FIG. 5A is a lateral view of the guide wire alignment system including the model of the scapula of FIG. 4A showing the guide plate of FIG. 1 coupled to the glenoid.

FIG. 5A is a lateral view of the guide wire alignment system 100 including the model 410 of the scapula of FIG. 4A showing the guide plate 120 of FIG. 1 coupled to the glenoid. In an example, the model 410 can include a first indicator 510 at a first location. The first indicator 510 can be included in the model 410 when the model 410 is manufactured. The first indicator 510 can be included in the model 410 after the model 410 has been manufactured, such as by a surgeon using a marker (e.g., a felt tipped permanent marker), or scribing the first indicator 510 into the model 410. In an example, the first indicator 510 corresponds with a second indicator (not shown) on an anatomical feature (not shown), such as a scapula or a hip bone. The model 410 can be a representation of the anatomical feature. The first location of the first indicator 510 can correspond with a second location of the second indicator. The model 410 can be an exact (or near exact) replica of the anatomical feature. The model 410 can reproduce or approximate surface features of the anatomical feature. The first indicator 510 and the second indicator can respectively be located in the exact same location on the model 410 and the anatomical feature of which the model 410 replicates.

In an example, the model 410 can be coupled with a second guide wire 430. The second guide wire 430 can be located at a model axis of the model 410. In an example, the guide plate 120 can include a first guide wire bore 230. The second guide wire 430 can be translated through the first guide wire bore 230. As shown in FIG. 5A, a diameter of the first guide wire bore 230 can be greater than a diameter of the second guide wire 430. The guide plate 120 can be placed in communication with, or couple with, the model 410. In an example, the guide plate 120 can include the alignment indicia 210. In an example, the alignment indicia 210 can be aligned with the first indicator 510 of the model 410 and the first indicator 510 corresponds in location to a second indicator (not shown) on an anatomical feature that the model 410 represents. The first indicator 510 and the alignment indicia 210 can be used as a reference for orientating the guide plate 120 with respect to the model 410. Using the first indicator 510 and the alignment indicia 210 as a reference on the model 410, can allow for the guide plate 120 to be orientated in the same manner with respect to the anatomical feature of which the model 410 represents.

Figure 5B:
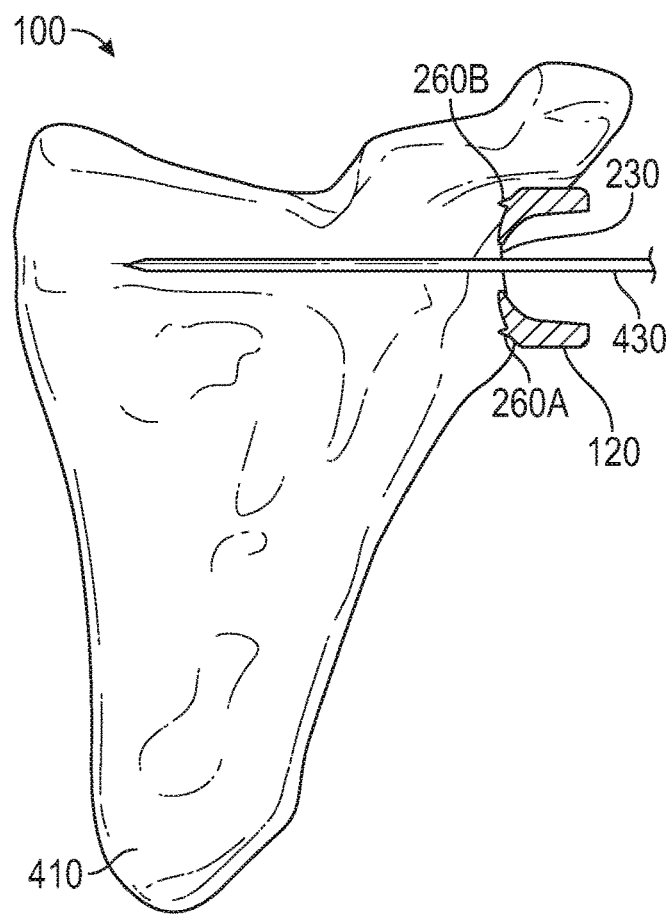
FIG. 5B is a posterior view of the guide wire alignment system including the model of the scapula of FIG. 5A showing the guide plate of FIG. 1 coupled to the glenoid.

FIG. 5B is a posterior view of the guide wire alignment system 100 including the model 410 of the scapula of FIG. 5A showing the guide plate 120 of FIG. 1 coupled to the glenoid. FIG. 5B shows the second guide wire 430 coupled with, and extending from, the model 410. The second guide wire 430 can extend through the first guide wire bore 230. The guide plate surface features 260A and 260B can be in communication with the model 410. The guide plate surface features 260A and 260B can improve the coupling of the guide plate 120 with the model 410, or with an anatomical feature (not shown).

Figure 6:
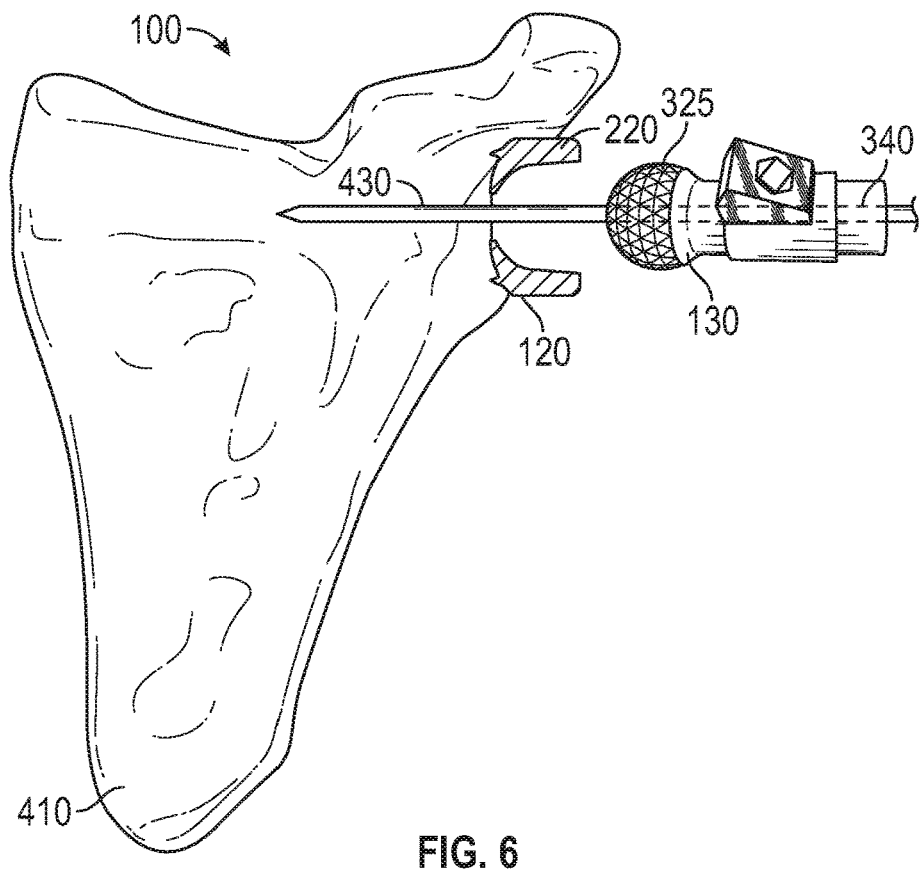
FIG. 6 is a posterior view of the guide wire alignment system including the model of the scapula of FIG. 5B showing the axis guide of FIG. 1 translating over a second guide wire.
Figure 9:
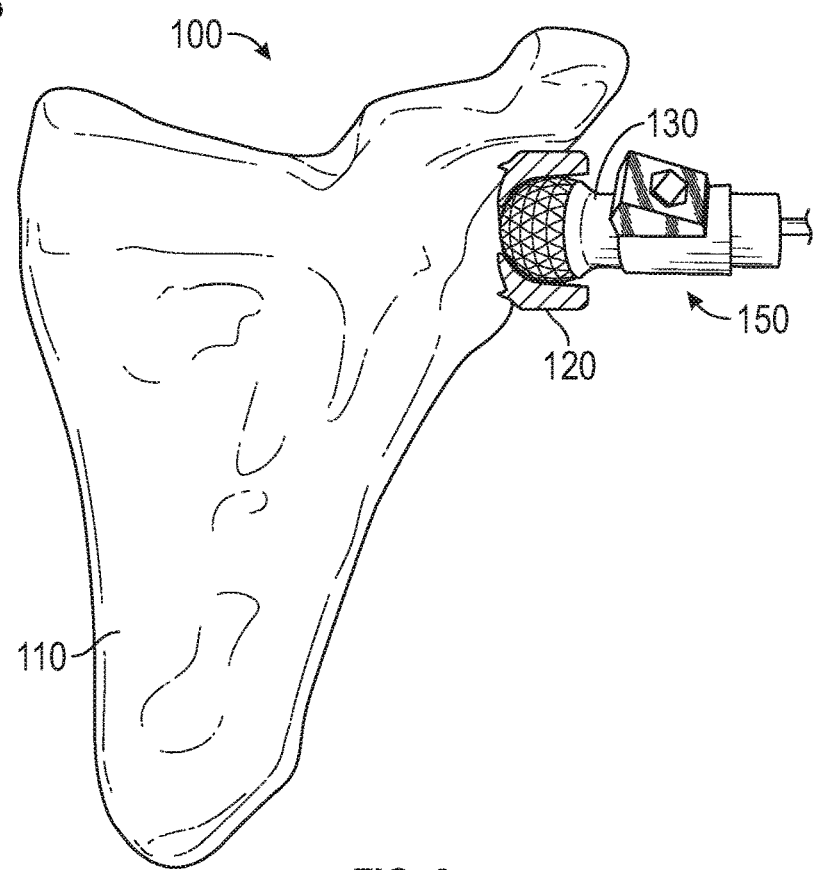
FIG. 9 is posterior view of an example of the guide wire alignment system including the scapula of FIG. 8 showing an example of the alignment unit of FIG. 1 mated with an anatomical feature.

FIG. 6 is a posterior view of the guide wire alignment system 100 including the model 410 of the scapula of FIG. 5B showing the axis guide 130 of FIG. 1 translating over a second guide wire 430. In an example, the second guide wire 430 can be coupled with, and extend from, a model 900. Although the second guide wire 430 shown in FIG. 9 is horizontal (e.g., parallel with the top and bottom edges of the sheet), the second guide wire 430 can be positioned in other orientations. The orientation at which the second guide wire 430 extends from the model 900 can be dependent upon the location and orientation of a model axis of the model 900 and can be determined by the surgeon preoperatively after analyzing the anatomy. In an example, the axis guide 130 can include a second guide wire bore 932. The second guide wire bore 932 can be configured to allow the axis guide 130 to translate along the second guide wire 945. The second guide wire bore 932 can be configured to allow the second guide wire 430 to translate through the axis guide 130 in a single orientation.

Figure 7:
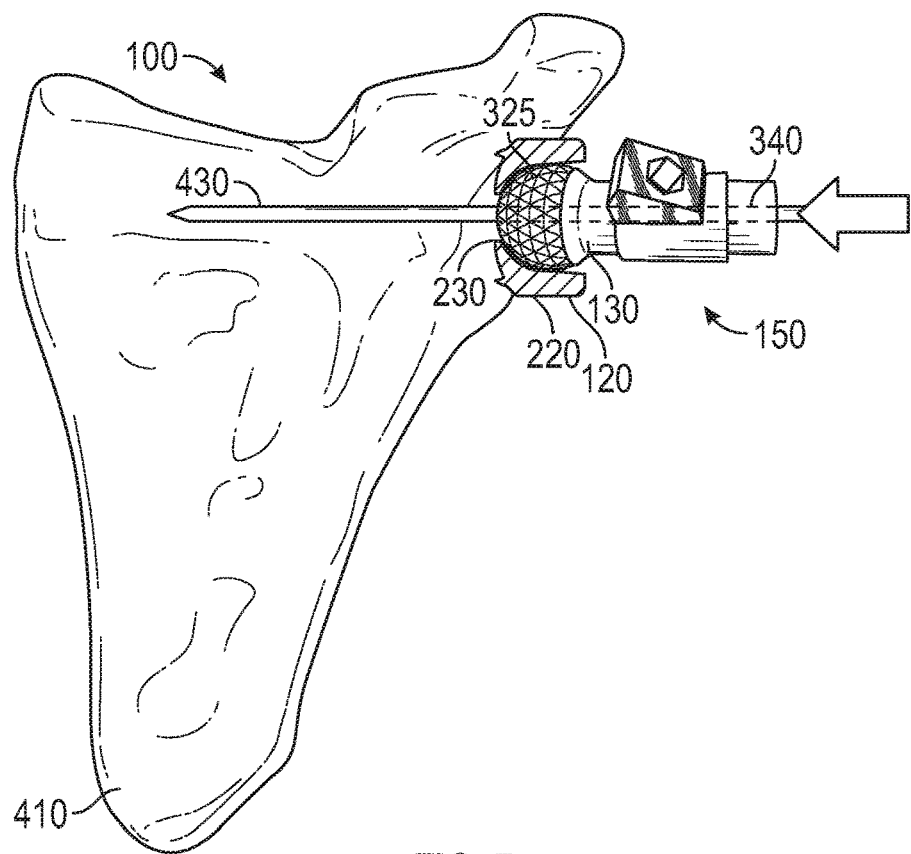
FIG. 7 is a posterior view of the guide wire alignment system including the model of the scapula of FIG. 6 showing the axis guide coupled with the guide plate.

FIG. 7 is a posterior view of the guide wire alignment system 100 including the model 410 of the scapula of FIG. 6 showing the axis guide 130 coupled with the guide plate 120. In an example, the axis guide 130 can be configured to mate, or couple, with the guide plate 120. The mating of the axis guide 130 with the guide plate 120 can allow for the fixable positioning of the axis guide 130 relative to the guide plate 120. In an example, the second guide wire 430 can extend through a first guide wire bore 230 of the guide plate 120. The second guide wire 430 can be inserted into a second guide wire bore 340 of the axis guide 130. The axis guide 130 can then be translated over the second guide wire 430 and a head 1033 of the axis guide 130 can be inserted into the socket 220. As discussed herein, the first guide wire bore 230 can be configured to allow the second guide wire 430 to translate through the first guide wire bore 230 in one or more orientations. The second guide wire bore 340 can be configured to allow the second guide wire 430 to translate through the second guide wire bore 340 in a single orientation. As the axis guide 130 is translated over the second guide wire 430 and inserted into the socket 220, the second guide wire 430 can orientate the axis guide 130 relative to the guide plate 120.

In an example, the second guide wire 430 can extend from the guide plate 120 at a 10 degree angle relative to the model axis 420. As the axis guide 130 is translated over the second guide wire 430 and engages with the socket 1030, the axis guide can take on the 10 degree angle because the axis guide 130 can be configured to translate over the second guide wire 430 in only a single orientation. The fixable positionability of the axis guide 130 relative to the guide plate 120 can allow for the axis guide 130 to remain at the 10 degree angle relative to the guide plate 120 when the axis guide 130 and the guide plate 120 are removed (e.g., decoupled) from the second guide wire 430 (and/or the model 410) as a mated alignment unit (e.g., the head 1033 remains within the socket 220). Although a 10 degree angle between the axis guide 130 and the guide plate 120 (and the second guide wire 430) is discussed, other orientations and/or relative angles are able to be used/configured.

Figure 8:
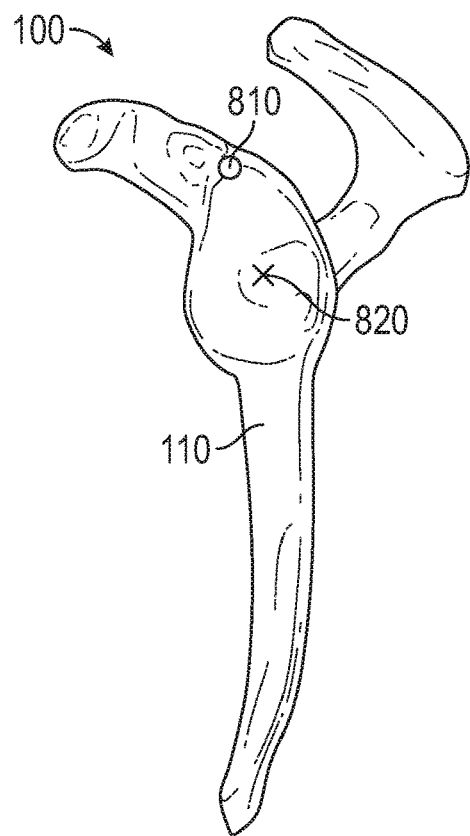
FIG. 8 is a lateral view of an example of the guide wire alignment system showing an example of an anatomical feature relative to an alignment axis.

FIG. 8 is a lateral view of an example of the guide wire alignment system 100 showing an example of an anatomical feature relative to an alignment axis. In an example, the anatomical feature 110 can be a scapula. In another example, the anatomical feature 110 can be a hip bone. In an example, the anatomical feature can be a joint (or a portion of a joint) within the human body. The anatomical feature 110 can include an anatomical axis 820. In an example, the anatomical axis 820 can be a transverse scapular axis. The anatomical axis 820 can be defined by the anatomical landmarks of the anatomical feature 110, independent of the position of the anatomical feature 110 within the human frame. The anatomical feature 110 can include a second indicator 810 located at a second location. The second location of the second indicator 810 can correspond with a first location of a first indicator (e.g., the first indicator 510 of FIG. 5A). In an example, a model (e.g., the model 410 of FIGS. 4A, 4B, and 4C) can be manufactured as a representation of the anatomical feature 110. The location of the anatomical axis 820 in the anatomical feature 110 can correspond in location with a model axis (e.g., the model axis 420 of FIGS. 4A, 4B, and 4C) of the model.

FIG. 9 is posterior view of an example of the guide wire alignment system 100 including the scapula of FIG. 8 showing an example of the alignment unit 150 of FIG. 1 mated with an anatomical feature 110. The alignment unit 150 can be referred to as a mated alignment unit. The alignment unit 150 can be used to couple a first guide wire (not shown) with the anatomical feature 110. The alignment unit 150 can be used to locate the first guide wire 140 at an anatomical axis (e.g., the anatomical axis 820 of FIG. 11) of an anatomical feature. The alignment unit 150 can assist in accurately and precisely placing the first guide wire at the anatomical axis of the anatomical feature 110.

The alignment unit 150 can allow for an individual (e.g., a surgeon, nurse, or the like) to establish the relative angles of the axis guide 130 to the guide plate 120 with a model (e.g., the model 410 of FIGS. 4A, 4B, and 4C) outside of a patient. Establishing the relative angles with the model can simplify installation of a replacement anatomy (e.g., a femoral head or a humerus head) by simplifying the identification of a mounting location (e.g., the anatomical axis) for the replacement anatomy. Establishing the relative angles with the model can simplify installation of the replacement anatomy by eliminating obstructions (e.g., other anatomical features) while identifying the mounting location for the replacement anatomy.

Figure 11:
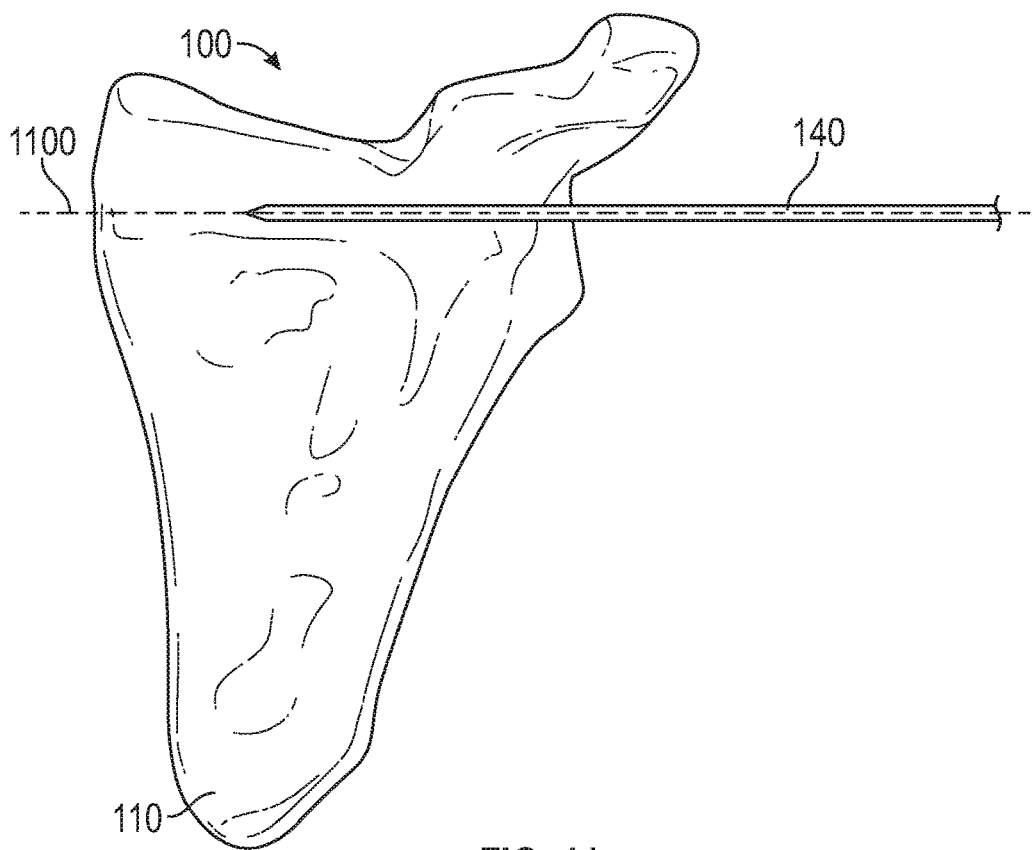
FIG. 11 is a posterior view of an example of the guide wire alignment system including the first guide wire of FIG. 10 installed in an anatomical feature.

In an example, coupling the alignment unit 150 with the anatomical feature 110 can include aligning an alignment indicia (e.g., the alignment indicia 210 of FIGS. 2A and 2B) of the guide plate 120 with a second indicator (e.g., the second indicator 810 of FIG. 11). Aligning the alignment indicia with the second indicator can ensure that the alignment unit 150 is properly oriented with respect to the anatomical feature 110. Proper orientation of the alignment unit 150 with respect to the anatomical feature 110 can be important because the alignment unit 150 can have the orientation of the axis guide 130, with respect to the guide plate 120, established with a model. If a model is used to establish the relative angles between the axis guide 130 and the guide plate 120, proper orientation of the alignment unit 150 with respect to the anatomical feature 110 can allow for a first guide wire to be located in the anatomical feature 110 at the same location as a second guide wire that was installed in the model. The alignment unit 150 can be used to place the first guide wire or the second guide wire.

Figure 10:
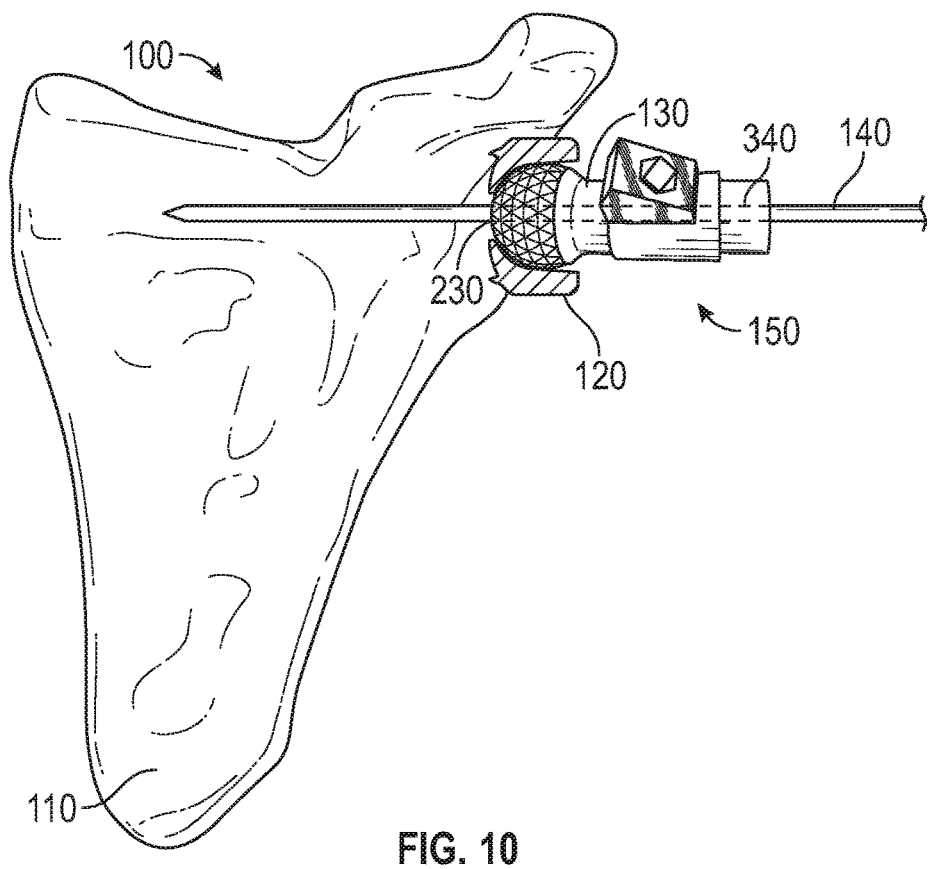
FIG. 10 is a posterior view of an example of the guide wire alignment system including a first guide wire installed in an anatomical feature through the use of an alignment unit.

FIG. 10 is a posterior view of an example of the guide wire alignment system 100 including a first guide wire 140 installed in an anatomical feature 110 through the use of an alignment unit 150. In an example, the alignment unit 150 can be configured to allow for the fixable positioning of the axis guide 130 relative to the guide plate 120. The position, or orientation, of the axis guide 130 with respect to the guide plate 120 can be established with a model (e.g., the model 410 of FIGS. 4A, 4B, and 4C). The positioning can include using a second guide wire (e.g., the second guide wire 430 of FIGS. 4A, 4B, and 4C) to orientate the axis guide with respect to the guide plate 120. The alignment unit 150 can then decoupled from the second guide wire and/or the model.

An individual (e.g., a surgeon, nurse, or the like) can couple the alignment unit 150 to the anatomical feature 110, including properly orientating the alignment unit 150 with respect to the anatomical feature 110. The individual can then translate the first guide wire 140 through the second guide wire bore 340. The second guide wire bore 340 can be configured to allow the first guide wire 140 to translate through the second guide wire bore 340 in a single orientation. The translation of the first guide wire 140 through the second guide wire bore 340 and the first guide wire bore 230 can place the first guide wire 140 at an anatomical axis (e.g., the anatomical axis 820 of FIG. 11).

The first guide wire 140 can be placed at the anatomical axis because the alignment unit 150 had its relative angles set by the model. The second guide wire was placed at a model axis (e.g., the model axis 420 of FIGS. 4A, 4B, and 4C) and the model axis can correspond in location and orientation with the anatomical axis. The model can be a replica or representation of the anatomical feature 110, so the fixable positioning of the alignment unit 150 can allow for the orientation of the second guide wire, with respect to the model, to be translated (e.g., copied or reproduced) to the anatomical feature 110 and can allow for the first guide wire 140 to be placed along the anatomical axis.

In an example, the guide plate 120 and the axis guide 130 are decoupled from the anatomical feature 110. In an example, the guide plate 120 and the axis guide 130 are decoupled from a first anatomical feature of a first patient. The guide plate 120 and the axis guide 130 can be sanitized. The guide plate 120 and the axis guide 130 can be coupled to a second anatomical feature of the first patient. The guide plate 120 and the axis guide 130 can be coupled to a second anatomical feature of a second patient. The first anatomical feature can be the same as the second anatomical feature.

The first anatomical feature can be different than the second anatomical feature. The guide plate 120 and the axis guide 130 can be coupled to additional anatomical features of additional patients.

FIG. 11 is a posterior view of an example of the guide wire alignment system 100 including the first guide wire 140 of FIG. 10 installed in an anatomical feature 110. In an example, the first guide wire 140 can have a longitudinal axis. In an example, the longitudinal axis can be collinear with an anatomical axis 820 of the anatomical feature 110. In an example, the first guide wire 140 can be located in substantially the same location and orientation as a second guide wire (e.g., the second guide wire 430 of FIGS. 4A, 4B, and 4C). Stated another way, the position and orientation of the first guide wire 1445 can replicate the position and orientation of the second guide wire.

As shown in FIG. 4A, a model 410 of the anatomy of a patient can be obtained or manufactured using medical imaging of the patient anatomy. An individual can locate the model axis 420 in the model 410. The model axis 420 can correspond to an anatomical axis (e.g., the anatomical axis 820 of FIG. 11) of the anatomical feature. As shown in FIGS. 4B and 4C, an individual can place a second guide wire 430 in the model 410 along the model axis 420. Placing the guide wire along the model axis 420 can be used in order to avoid misalignment of the guide wire in the anatomy. For example, when the model axis 420 corresponds to the anatomical axis 820 of the anatomical feature the first guide wire will not errantly protrude from the anatomy. As shown in FIGS. 5A and 5B, an individual can couple the guide plate 120 to the second guide wire 430 and the model 410. The individual can align the guide plate 120 with the anatomical feature by aligning the alignment indicia 210 with the first indicator 510. The second guide wire 430 can translate through the first guide wire bore 230 of the guide plate 120 in one or more orientations.

As shown in FIGS. 6 and 7, the axis guide 130 can be coupled to the guide plate 120. The coupling of the axis guide 130 can include translating the second guide wire 430 through a second guide wire bore 340 of the axis guide 130. The guide plate 120 and the axis guide 130 can be decoupled as an alignment unit 150 from the second guide wire 430. As shown in FIG. 8, the anatomical feature 110 can include a second indicator 810 and the anatomical axis 820. As shown in FIG. 9, the guide plate 120 and the axis guide 130 can be coupled to the anatomical feature 110 as an alignment unit 150. As shown in FIGS. 10 and 11, the alignment unit 150 can be used to place the first guide wire 140 in the anatomical feature 110 of the patient. The fixable positioning of the axis guide 130 with the guide plate 120 can allow for the first guide wire 140 to be located at the anatomical axis 820 of the anatomical feature 110. The fixable positioning of the axis guide 130 with the guide plate 120 can allow for the longitudinal axis of the first guide wire 140 to be collinear with the anatomical axis 820 of the anatomical feature 110.

Use of the alignment unit 150 can allow for first and second standard (e.g., components that are not fabricated specifically for a patient) components (e.g., the axis guide 130 and the guide plate 120) to be use to make a semi-patient-specific assembly of the first and second standard components. A patient specific model can be used to set the relative angles between the first and second standard components and give the first and second standard components a semi-patient-specific configuration. However, a model need not always be used to set the relative angles between the first and second standard components. The relative angles between the first and second components can also be established using a third standard component. The relative angles can be determined using medical imaging and the third standard component can be used to establish the relative angles of the first and second standard components.

Figure 12:
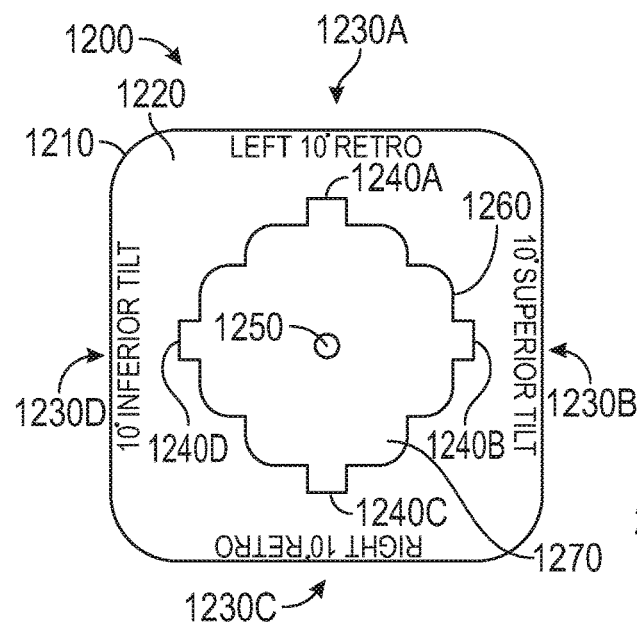
FIG. 12 is a top view of another example of a guide wire alignment system including a guide cube.

FIG. 12 is a top view of another example of a guide wire alignment system 1200 including a guide cube 1210. In an example, the guide cube 1210 can be used to set relative angles between a guide plate (e.g., the guide plate 120 of FIG. 1) and an axis guide (e.g., the axis guide 130 of FIG. 1) In an example, the guide cube 1210 can include a face 1220, a slot 1260, a base portion 1270, a third guide wire bore 1250, one or more cube indicia 1230A, 1230B, 1230C, and 1230D, a first indicator 1240A, a second indicator 1240B, a third indicator 1240C, and a fourth indicator 1240D. In an example, the face 1220 can be one of a plurality of faces of the guide cube 1210. In an example, the face 1220 can be one of six faces of the guide cube 1210.

In an example, the face 1220 can include the slot 1260. In an example, each of the faces of the plurality of faces respectively include a slot (e.g., the slot 1260). The first, second, third, and fourth indicators 1240A, 1240B, 1240C, and 1240D can be integral with the slot 1260. In an example, the slot 1260 can include the base portion 1270. In an example, the slot 1260 can be configured to receive the guide plate. In an example, the slot 1260 can be configured to receive the guide plate in a plurality of orientations. The reception of the guide plate by the slot 1260 can mate the guide plate with the base portion 1270 of the slot 1260. In an example, the third guide wire bore 1250 can be included in a plurality of guide wire bores. The third guide wire bore 1250 can extend from the face 1220 to another face located on the opposite side of the guide cube 1210. Other guide wire bores of the plurality of guide wire bores can extend through the guide cube 1210 orthogonally to the face 1220. The third guide wire bore 1250 can be configured to receive a second guide wire (not shown) in a single orientation. The second guide wire can extend orthogonally from the face 1220.

In an example, the base portion 1270 of the slot 1260 can be configured as an inclined plane. Stated another way, the bottom (e.g., the base portion 1270) of the slot 1260 can be angled such that a first distance from a first side of the slot 1260 to the face 1220 can be different than a second distance from the bottom of a second side of the slot 1260 to the face 1220. Stated yet another way, the depth of the slot 1260 relative to the face 1220 can vary over the area of the slot 1260. The base portion 1270 of the slot 1260 can be configured to include a plurality of inclined planes. The inclined plane can have an angular slope from a first end of the inclined plane to a second end of the inclined plane. The one or more cube indicia 1230A, 1230B, 1230C, and 1230D can be used to identify the angular slope of the inclined plane. The one or more cube indicia 1230A, 1230B, 1230C, and 1230D can respectively be aligned with the first, second, third, and fourth indicators 1240A, 1240B, 1240C, and 1240D.

Figure 13:
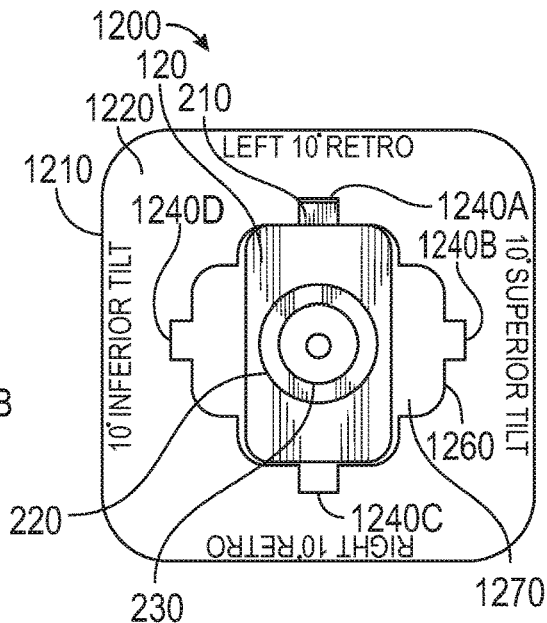
FIG. 13 is a top view of the guide wire alignment system of FIG. 12 showing the guide plate of FIG. 1 mated with the guide cube.

FIG. 13 is a top view of the guide wire alignment system 1200 of FIG. 12 showing the guide plate 120 of FIG. 1 mated with the guide cube 1210. In an example, the guide plate 120 can include an alignment indicia 210, and a socket 220. In an example, the guide cube 1210 can include a face 1220, a slot 1260, a base portion 1270, a third guide wire bore 1605, a first indicator 1240A, a second indicator 1240B, a third indicator 1240C, and a fourth indicator 1240D.

The alignment indicia 210 of the guide plate 120 can be used to orientate the guide plate 120 with respect to the guide cube 1210. The alignment indicia 210 can be used to orientate the guide plate 120 with respect to an anatomical feature (not shown). In an example, aligning the alignment indicia 210 with the first indicator 1240A and placing the guide plate 120 within the slot 1260 (e.g., mating the guide plate 120 with the slot 1260) results in the guide plate 120 being angled at a 10 degree angle relative to the face 1220 of the guide cube 1210. In another example, aligning the alignment indicia 210 with the second indicator 1240B and placing the guide plate 120 within the slot 1260 results in the guide plate 120 being angled at a 10 degree angle relative to the face 1220 of the guide cube 1210. However, by aligning the alignment indicia 210 with the second indicator 1240B instead of the first indicator 1240A, the 10 degree angle relative to the face 1220 will be reoriented into a different orientation with respect to the guide cube 1210. Stated another way, aligning the alignment indicia 210 with the second indicator 1240B instead of the first indicator 1240A can allow for the guide plate 120 to be oriented at a 10 degree angle with respect to the face 1220, but the direction of the tilt will differ depending upon the orientation of the guide plate 120 within the slot 1260.

In an example, the alignment indicia 210 can be positioned in the superior direction when the guide plate 120 is coupled with an anatomical feature (e.g., anatomical feature 110 of FIG. 1) of a patient. The base portion 1270 can be at an angle with respect to the face 1220. In the example of FIG. 13, the base portion 1270 can slope downward at a 10 degree angle from left to right (e.g., the right side of the base portion 1270 will have a greater depth than the left side of the base portion 1270). In an example, a medical practitioner is operating on a patient's left-side scapula. Placing the guide plate 120 within the slot 1260 such that the alignment indicia 210 is aligned with the first indicator 1240A, can result in the guide plate 120 having 10 degrees of retroversion tilt when coupled to the left-side scapula. However, if the guide plate 120 were coupled to a right-side scapula, the guide plate 120 would have 10 degrees of anteversion tilt. Furthermore, if the guide plate 120 were positioned so that the alignment indicia 210 is aligned with third indicator 1240C, the guide plate 120 would be configured to provide 10 degrees retroversion tilt for a right shoulder.

Placing the guide plate 120 within the slot 1260 such that the alignment indicia 210 is aligned with the second indicator 1240B, can result in the guide plate 120 having 10 degrees of superior tilt when coupled to the left-side scapula. Placing the guide plate 120 within the slot 1260 such that the alignment indicia 210 is aligned with the fourth indicator 1240D can result in the guide plate 120 having 10 degrees of inferior tilt when coupled to the left-side scapula. Because the inferior/superior relationship is unaffected by which side of the body an anatomical feature is located on, the guide plate 120 can have 10 degrees of inferior tilt or superior tilt when coupled to a right-side, or a left-side scapula when using indicators 1240D and 1240B, respectively.

Figure 14:
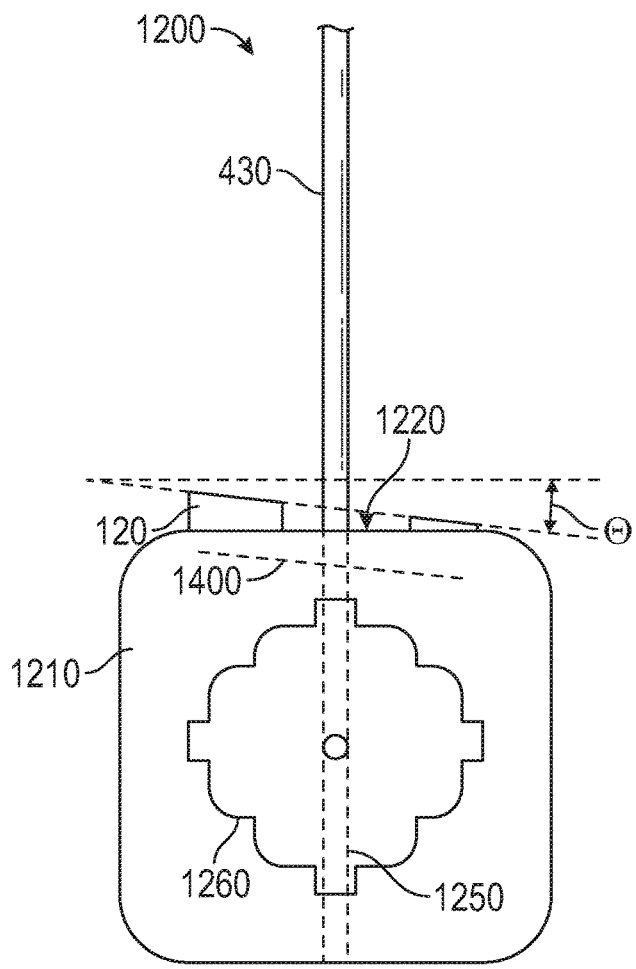
FIG. 14 is a side view of the guide wire alignment system of FIG. 13 showing a second guide wire extending from the guide cube.

FIG. 14 is a side view of the guide wire alignment system 1200 of FIG. 13 showing a second guide wire 430 extending from the guide cube 1210. In an example, the second guide wire 430 can be inserted into a third guide wire bore 1250 of the guide cube 1210. The second guide wire 430 can be translated through a first guide wire bore (not shown) of the guide plate 120 and the guide plate 120 can then be mated with the guide cube 1210. The guide plate 120 can be mated with the guide cube 1210 before the second guide wire 430 is mated with the guide cube 1210.

As previously discussed, the second guide wire 430 can extend orthogonally from a face 1220 of the guide cube 1210. The guide cube 1210 can have one or more slots, such as a slot 1260. The one or more slots can be configured to have one or more inclined planes, such as inclined plane 1400. In an example, the guide plate 120 and the second guide wire 430 can be mated with the guide cube 1210. The second guide wire 430 extends orthogonally from the face 1220 and through the first guide wire bore (not shown) of the guide plate 120. The guide plate 120 can be mated with the inclined plane 1400 of a slot. The inclined plane 1400 imparts an angle Θ to the guide plate 120 relative to the face 1220. The relative angle Θ between the guide plate 120 and the face 1220 can be the same as the relative angle between the guide plate 120 and the second guide wire 430. The second guide wire 430 can be able to extend through the guide plate 120 at an angle because the first guide wire bore (not shown) of the guide plate 120 can be configured to allow the second guide wire 430 to translate through the guide plate 120 in one or more orientations.

Figure 15:
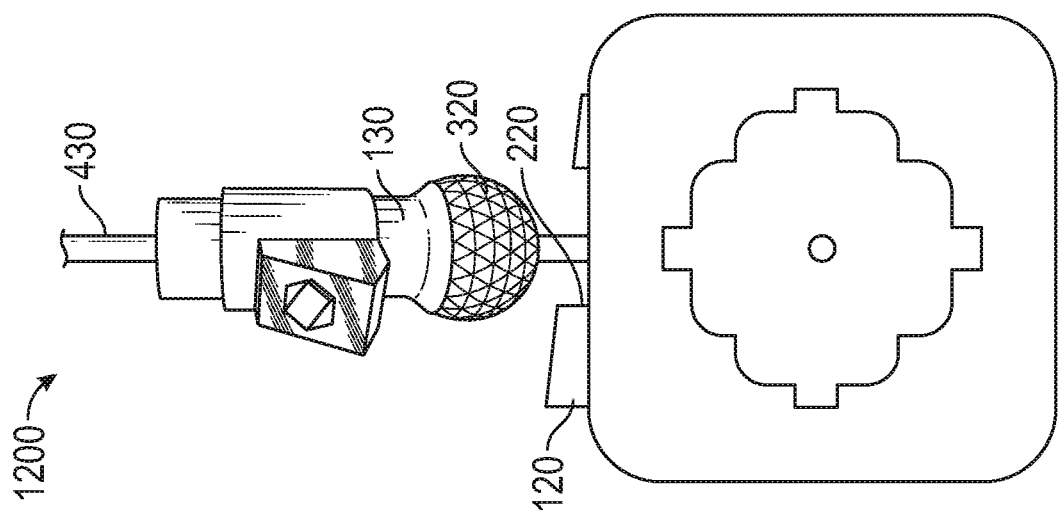
FIG. 15 is a side view of the guide wire alignment system of FIG. 14 showing the axis guide of FIG. 1 translating over the second guide wire.

FIG. 15 is a side view of the guide wire alignment system 1200 of FIG. 14 showing the axis guide 130 of FIG. 1 translating over the second guide wire 430. In an example, a guide plate 120 can be mated with a guide cube 1210 and the second guide wire 430 can be mated with the guide cube and translated through the guide plate 120. The guide plate has an angle relative to the guide cube 1210. The guide plate 120 has an angle (e.g., 1, 2, 5, 10, 15, or 25 degrees) relative to the second guide wire 430.

The axis guide 130 can include a second guide wire bore (not shown). The second guide wire bore can be configured to receive a guide wire (e.g., the second guide wire 430) in a single orientation (e.g., the axis guide can be able to translate or slide along the guide wire). The reception of the guide wire by the axis guide can make a longitudinal axis of the guide wire collinear with a longitudinal axis of the second guide wire bore.

The axis guide 130 can include a head 320. The head 320 can be configured to mate with, or couple with, a socket 220 of the guide plate 120. The mating of the head 320 and the socket 220 can allow for a fixable positioning of the axis guide 130 relative to the guide plate 120. In an example, the guide plate 120 can be mated with a slot (not shown) of the guide cube 1210 and can be oriented at a first angle with respect to a face of the guide cube 1210. The relative angle between the axis guide 130 and the guide plate 120 can be the first angle when a guide cube can be used in combination with the guide plate 120 and the axis guide 130. The axis guide 130 can be translated along the second guide wire 430 and brought into communication with the socket of the guide plate 120. The axis guide 130 can require a predetermined force (e.g., a surgeon applying a force, such as a hammer strike, to an end of the axis guide 130) to mate, or couple, the axis guide 130 with the guide plate 120.

The positionable mating of the axis guide 130 and the guide plate 120 can allow for the position, or orientation, of the axis guide 130 relative to the guide plate 120 to remain temporarily fixed, or unchanged, once the position or orientation has been established or set, such as by a surgeon using a guide cube 1210. Because the axis guide was translated over the second guide wire 430 and the second guide wire 430 can be at the first angle relative to the guide plate, the positionable mating of the axis guide 130 with the guide plate 120 can set the relative angles between the axis guide 130 and the guide plate 120 at the first angle. The axis guide 130 and the guide plate 120 can have more than one relative angle set. In an example, the first angle can be in a first plane. The axis guide 130 and the guide plate 120 can be set at a second angle along a second plane. The first plane can be different than the second plane. The first plane can be orthogonal to the second plane. Additional relative angles and planes are capable of being used with the axis guide 130 and the guide plate 120. The mated (e.g., coupled) axis guide 130 and the guide plate 120 can be removed (e.g., decoupled) from the guide cube 1210 and the second guide wire 430 as an alignment unit. The alignment unit can maintain the relative angles between the axis guide 130 and the guide plate 120 that were set using the guide cube 1210.

Figure 16:
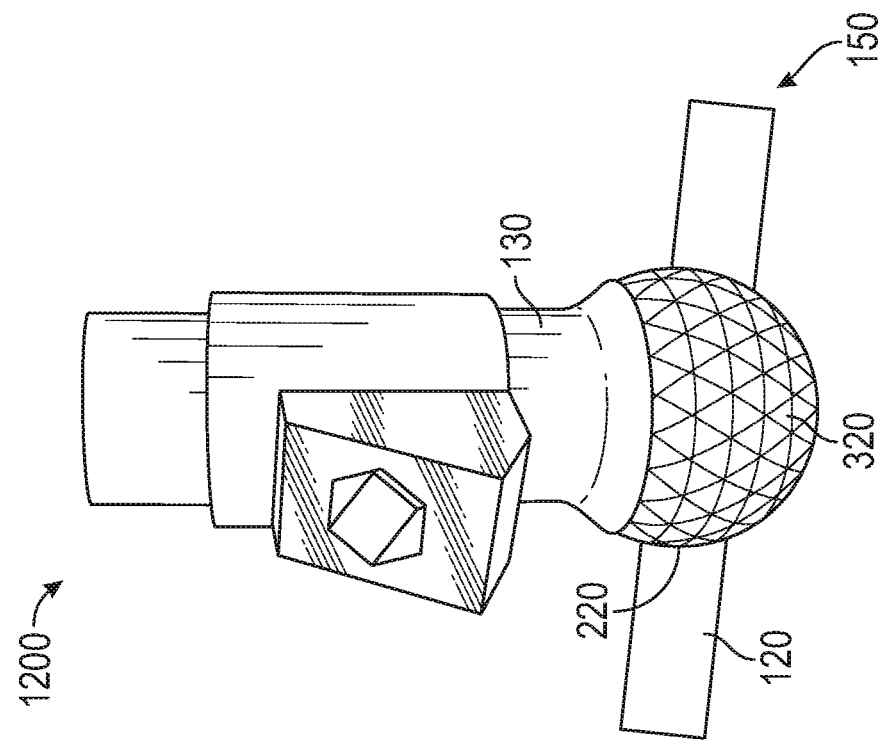
FIG. 16 is a schematic view of the guide wire alignment system showing the axis guide mated with the guide plate.

FIG. 16 is a schematic view of the guide wire alignment system 1200 showing the axis guide 130 mated with the guide plate 120. The alignment unit 150 can include an axis guide 130 and a guide plate 120. The relative angles between the axis guide 130 and the guide plate 120 can remain fixed once they have been set, such as through the interaction of one or more surface features on a head 320 of the axis guide and a socket 220 of the axis guide 120. In an example, the alignment unit 150 can be used to install a first guide wire in a patient's anatomical feature. As discussed herein, the alignment unit 150 can allow for a first guide wire to be installed at the relative angles that were established between the axis guide 130 and the guide plate 120.

As previously discussed, an individual (e.g., a radiologist, a surgeon, a nurse, or the like) can determine the anatomical geometry of a patient by performing medical imaging on an anatomical feature of the patient. In an example, x-ray images can be taken of the anatomical feature in various reference plan views (e.g., superior, anterior, medial, or the like). The anatomical geometry, such as the angular relationship of the anatomical feature with respect to another anatomical feature or the reference plan views, can be determined by the individual from the x-rays. The individual can use the guide cube 1210 to establish the relative angles between the guide plate 120 and the axis guide 130. The relative angles can be substantially similar (e.g., within 10 degrees) to the angular relationship determined from the x-rays. Use of x-rays and the guide cube 1210 can eliminate the need for more expensive forms of medical imaging. Use of x-rays and the guide cube 1210 can eliminate the need for fabricating a patient specific model (e.g., the model 410 of FIG. 4A) of the anatomical feature. Fabrication of the patient specific model can be expensive.

Additionally, the guide cube 1210 can be included in a set of guide cubes. The set of guide cubes can have different combinations of superior, inferior, anteversion and retroversion settings. In an example, the inclined plane 1400 of FIG. 14 can impart an angle Θ to the guide plate 120 relative to the face 1220. The angle Θ can vary depending upon what face of the guide cube 1210 is used (e.g., Θ is 10 degrees for the face 1220, but Θ for the other faces of guide cube 1210 will be greater than, or less than, 10 degrees). The angle Θ can vary depending upon which guide cube is used in the set of guide cubes (e.g., Θ is 10 degrees for the guide cube 1210, but Θ for other guide cubes will be greater than, or less than, 10 degrees). The angle Θ can vary in increments of 0.25 degrees, 0.5 degrees, 1 degree, 5 degrees, or 10 degrees, but other increments are possible. The guide cube 1210, or the set of guide cubes, can be used with a first patient and reused with subsequent patients after sanitizing.

VARIOUS NOTES & EXAMPLES

Aspect 1 can include or use subject matter (such as an apparatus, a system, a device, a method, a means for performing acts, or a device readable medium including instructions that, when performed by the device, can cause the device to perform acts), such as can include or use a method for placing a first guide wire in a patient. Aspect 1 can include or use locating a model axis in a model, the model axis corresponding to an anatomical axis of an anatomical feature of the patient. Aspect 1 can also include placing a second guide wire in the model located at the model axis. Aspect 1 can further include or use coupling a guide plate to the second guide wire and the model, wherein the guide plate includes a first guide wire bore. Aspect 1 can still further or use include coupling an axis guide to the guide plate, wherein coupling the axis guide includes translating the second guide wire through a second guide wire bore of the axis guide. Additionally, Aspect 1 can include or use decoupling the guide plate and the axis guide as an alignment unit from the second guide wire. Aspect 1 can further include or use coupling the guide plate and the axis guide as an alignment unit to the anatomical feature of the patient. Aspect 1 can still further include or use placing the first guide wire in the anatomical feature of the patient, wherein the coupling of the axis guide with the guide plate allows the first guide wire to be located at the anatomical axis of the anatomical feature.

Aspect 2 can include or use, or can optionally be combined with the subject matter of Aspect 1, to optionally include or use decoupling the guide plate and the axis guide from the anatomical feature.

Aspect 3 can include or use, or can optionally be combined with the subject matter of one or any combination of Aspects 1 or 2 to optionally include or use that the anatomical feature is a glenoid or an acetabulum.

Aspect 4 can include or use, or can optionally be combined with the subject matter of one or any combination of Aspects 1 through 3 to optionally include or use identifying an anatomical geometry of an anatomical feature of the patient, wherein the geometry of the anatomical feature includes an anatomical axis.

Aspect 5 can include or use, or can optionally be combined with the subject matter of one or any combination of Aspects 1 through 4 to optionally include or use fabricating the model of the anatomical feature including a model geometry, the model geometry corresponding to the anatomical geometry of the anatomical feature of the patient.

Aspect 6 can include or use, or can optionally be combined with the subject matter of one or any combination of Aspects 1 through 5 to optionally include or use fabricating the model includes fabricating the model by a process including machining, stereolithography, digital light processing, fused deposition modeling, selective laser sintering, selective laser melting, electronic beam melting, or laminated object manufacturing.

Aspect 7 can include or use, or can optionally be combined with the subject matter of one or any combination of Aspects 1 through 6 to optionally include or use identifying the anatomical geometry of the anatomical feature includes determining the anatomical geometry by performing medical imaging of the anatomical feature, the medical imaging including x-ray, magnetic resonance imaging, computed tomography scan, or ultrasound.

Aspect 8 can include or use, or can optionally be combined with the subject matter of one or any combination of Aspects 1 through 7 to optionally include or use placing the first guide wire or the second guide wire includes mechanically fastening the first guide wire or the second guide wire to the anatomical feature or the model, respectively.

Aspect 9 can include or use, or can optionally be combined with the subject matter of one or any combination of Aspects 1 through 8 to optionally include or use marking a first indicator on the model at a first location and marking a second indicator on the anatomical feature at a second location, wherein the first location corresponds with the second location.

Aspect 10 can include or use, or can optionally be combined with the subject matter of one or any combination of Aspects 1 through 9 to optionally include or use aligning one or more alignment indicia of the guide plate with the first indicator.

Aspect 11 can include or use, or can optionally be combined with the subject matter of one or any combination of Aspects 1 through 10 to optionally include or use aligning one or more alignment indicia of the guide plate with the second indicator.

Aspect 12 can include or use, or can optionally be combined with the subject matter of one or any combination of Aspects 1 through 11 to optionally include or use translating the first guide wire through the second guide wire bore in the axis guide and the first guide wire bore in the guide plate.

Aspect 13 can include or use, or can optionally be combined with the subject matter of one or any combination of Aspects 1 through 12 to optionally include or use a first guide wire bore that is greater than a diameter of the second guide wire bore.

Aspect 14 can include or use, or can optionally be combined with the subject matter of one or any combination of Aspects 1 through 13 to optionally include or use a first guide wire bore that is configured to allow the first or second guide wire to translate through the guide plate in one or more orientations.

Aspect 15 can include or use, or can optionally be combined with the subject matter of one or any combination of Aspects 1 through 14 to optionally include or use a second guide wire bore that is configured to allow the first or second guide wire to translate through the axis guide in a single orientation.

Aspect 16 can include or use, or can optionally be combined with the subject matter of one or any combination of Aspects 1 through 15 to optionally include or use axis guide is configured to couple with the guide plate at one or more orientations.

Aspect 17 can include or use, or can optionally be combined with the subject matter of one or any combination of Aspects 1 through 16 to optionally include or use that the patient is a first patient, and further including: sanitizing the guide plate and axis guide, and coupling the guide plate and axis guide to an anatomical feature of a second patient.

Aspect 18 can include or use subject matter (such as an apparatus, a system, a device, a method, a means for performing acts, or a device readable medium including instructions that, when performed by the device, can cause the device to perform acts), such as can include or use a guide wire placement apparatus. Aspect 18 can include or use a model including a model axis, wherein the model axis corresponds to an anatomical axis of an anatomical feature. Aspect 1 can also include or use a second guide wire coupled with the model at the model axis. Aspect 1 can further include or use a guide plate. The guide place can include or use a first guide plate surface configured to couple with an anatomical feature of a patient, a second guide plate surface opposite the first guide plate surface, a guide plate socket extending into the first guide plate surface, and a guide wire bore extending from the socket to the second guide plate surface to allow a guide wire to translate through the guide plate. Aspect 1 can still further include or use an axis guide. The axis guide can include or use a coupling member configured to lock into the socket in multiple positions, and a second guide wire bore passing through the axis guide, wherein the second guide wire bore is configured to allow the guide wire to translate through the second guide wire bore in one position. Aspect 1 can also include or use the positionable mating of the coupling member with the guide plate bore aligns the first guide wire bore with the second guide wire bore.

Aspect 19 can include or use, or can optionally be combined with the subject matter of Aspect 18, to optionally include or use that the anatomical feature is a scapula or a hip bone.

Aspect 20 can include or use, or can optionally be combined with the subject matter of one or any combination of Aspects 18 or 19 to optionally include or use that the guide plate includes an indicator, wherein the indicator is configured to be aligned with a portion of the anatomical feature.

Aspect 21 can include or use, or can optionally be combined with the subject matter of one or any combination of Aspects 18 through 20 to optionally include or use that the axis guide includes a mounting location, the mounting location used to couple with a handle.

Aspect 22 can include or use, or can optionally be combined with the subject matter of one or any combination of Aspects 18 through 21 to optionally include or use that the guide plate socket is tapered.

Aspect 23 can include or use, or can optionally be combined with the subject matter of one or any combination of Aspects 18 through 22 to optionally include or use that the first guide plate surface includes one or more surface features that are configured to increase the friction coefficient of the first guide plate surface.

Aspect 24 can include or use, or can optionally be combined with the subject matter of one or any combination of Aspects 18 through 23 to optionally include or use the coupling member is quasi-spherical, and the one or more surface features are in communication with a surface of the guide plate socket.

Aspect 25 can include or use subject matter (such as an apparatus, a system, a device, a method, a means for performing acts, or a device readable medium including instructions that, when performed by the device, can cause the device to perform acts), such as can include or use a system for placing a first guide wire in a patient. Aspect 25 can include or use a model including a model axis, wherein the model axis corresponds to an anatomical axis of an anatomical feature. Aspect 25 can also include or use a second guide wire coupled with the model at the model axis. Aspect 25 can further include a guide plate that can include: a first guide plate surface configured to couple with an anatomical feature of a patient, a second guide plate surface opposite the first guide plate surface, a guide plate socket extending into the first guide plate surface, and a guide wire bore extending from the socket to the second guide plate surface to allow a guide wire to translate through the guide plate. Aspect 25 can still further include an axis guide. The axis guide can include or use a coupling member configured to lock into the socket in multiple positions, and a second guide wire bore passing through the axis guide, wherein the second guide wire bore is configured to allow the guide wire to translate through the second guide wire bore in one position. Aspect 25 can also include the positionable mating of the coupling member with the guide plate bore aligns the first guide wire bore with the second guide wire bore.

Aspect 26 can include or use, or can optionally be combined with the subject matter of Aspect 25 to optionally include or use that the coupling member is quasi-spherical, and the one or more surface features are in communication with the walls of the guide plate socket.

Aspect 27 can include or use, or can optionally be combined with the subject matter of one or any combination of Aspects 25 or 26 to optionally include or use that the guide plate socket is tapered.

Aspect 28 can include or use, or can optionally be combined with the subject matter of one or any combination of Aspects 25 through 27 to optionally include or use that the alignment rig is configured to couple with the model and locate the model axis.

Aspect 29 can include or use, or can optionally be combined with the subject matter of one or any combination of Aspects 25 through 28 to optionally include or use that the model is an anatomy simulator configured for setting the relative angles.

Aspect 30 can include or use subject matter (such as an apparatus, a system, a device, a method, a means for performing acts, or a device readable medium including instructions that, when performed by the device, can cause the device to perform acts), such as can include or use a method for calibrating adjustable orthopaedic devices. Aspect 30 can include or use identifying an anatomical geometry of an anatomical feature of the patient, wherein the geometry of the anatomical feature includes an anatomical axis. Aspect 30 can also include or use coupling a first guide wire to an anatomy simulator, wherein the anatomy simulator is configured to reproduce the anatomical axis. Aspect 30 can further include coupling a guide plate with the anatomy simulator, wherein coupling the guide plate with the anatomy simulator includes translating the first guide wire through a first guide wire bore of the guide plate, the first guide wire bore configured to allow first guide wire to translate through the guide plate in one or more orientations. Aspect 30 can still further include coupling an axis guide to the guide plate, wherein coupling the axis guide includes translating the first guide wire through a second guide wire bore of the axis guide, the second guide wire bore configured to receive the first guide wire in a single orientation. Aspect 30 can also include decoupling the guide plate and the axis guide as a unit from the first guide wire. Aspect 30 can further include coupling the guide plate and the axis guide as a unit to the anatomical feature of the patient. Aspect 30 can still further include placing a second guide wire in the anatomical feature of the patient, wherein the coupling of the axis guide with the guide plate allows the second guide wire to be located at the anatomical axis of the anatomical feature.

Aspect 31 can include or use, or can optionally be combined with the subject matter of Aspect 30 to optionally include or use that the anatomy simulator includes one or more faces, wherein the faces include a simulator socket.

Aspect 32 can include or use, or can optionally be combined with the subject matter of one or any combination of Aspects 30 or 31 to optionally include or use that the anatomy simulator is a reproduction of the anatomical feature.

Aspect 33 can include or use subject matter (such as an apparatus, a system, a device, a method, a means for performing acts, or a device readable medium including instructions that, when performed by the device, can cause the device to perform acts), such as can include or use an anatomy simulator. Aspect 33 can include or use a guide body having one or more faces. Aspect 33 can also include or use a first simulator socket forming a recess in a first face of the one or more faces. The first simulator socket can be configured to receive a guide plate. The first simulator socket can include a base portion. Aspect 33 can further include or use a guide wire bore extending from the base portion of the first simulator socket to the interior of the anatomy simulator. The guide wire bore can be configured to receive a guide wire in a single orientation.

Aspect 34 can include or use, or can optionally be combined with the subject matter of Aspect 33 to optionally include or use that the first base portion is angled at a first angle with respect to the first face.

Aspect 35 can include or use, or can optionally be combined with the subject matter of one or any combination of Aspects 33 or 34 to optionally include or use simulator indicia on the first face configured to provide alphanumerical information identifying the first angle.

Aspect 36 can include or use, or can optionally be combined with the subject matter of one or any combination of Aspects 33 through 35 to optionally include or use that the first socket includes one or more indicator portions configured to receive an alignment indicia of a guide plate.

Aspect 37 can include or use, or can optionally be combined with the subject matter of one or any combination of Aspects 33 through 36 to optionally include or use that the first face includes a first simulator indicia configured to provide alphanumerical information identifying the first angle, the first simulator socket includes a first indicator portion configured to receive an alignment indicia of the guide plate, and wherein aligning the alignment indicia with the first indicator portion and mating the guide plate with the anatomy simulator imparts the first angle onto the guide plate with respect to the first face.

Aspect 38 can include or use, or can optionally be combined with the subject matter of one or any combination of Aspects 33 through 37 to optionally include or use that the guide wire bore is configured to extend orthogonally to the first face.

Aspect 39 can include or use, or can optionally be combined with the subject matter of one or any combination of Aspects 33 through 38 to optionally include or use that the first simulator socket is included in a plurality of simulator sockets and each of the one or more faces includes an individual simulator socket of the plurality of sockets.

Aspect 40 can include or use, or can optionally be combined with the subject matter of one or any combination of Aspects 33 through 39 to optionally include or use that the guide plat includes: a first guide plate surface configured to couple with an anatomical feature of a patient, a second guide plate surface opposite the first guide plate surface, a guide plate socket extending into the first guide plate surface, and a guide wire bore extending from the socket to the second guide plate surface to allow a guide wire to translate through the guide plate.

Each of these non-limiting examples can stand on its own, or can be combined in various permutations or combinations with one or more of the other examples.

The above detailed description can include references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" can include "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that can include elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method for placing a first guide wire in a patient, comprising:
    locating a model axis in a model, the model axis corresponding to an anatomical axis of an anatomical feature of the patient;
    placing a second guide wire in the model located at the model axis;
    coupling a guide plate to the second guide wire and the model, wherein the guide plate comprises:
        a first guide plate surface configured to couple with the anatomical feature;
        a second guide plate surface opposite the first guide plate surface;
        a guide plate socket extending into the first guide plate surface, wherein the guide plate socket includes one or more surface features that are configured to increase the friction coefficient of the guide plate socket; and
        a first guide wire bore extending from the guide plate socket to the second guide plate surface to allow a guide wire to translate through the guide plate;
    coupling an axis guide to the guide plate, the axis guide comprising:
        a coupling member configured to lock into the guide plate socket in multiple positions; and
        a second guide wire bore passing through the axis guide;
        wherein coupling the axis guide includes translating the second guide wire through a second guide wire bore of the axis guide;
    decoupling the guide plate and the axis guide as an alignment unit from the second guide wire;
    coupling the guide plate and the axis guide as an alignment unit to the anatomical feature of the patient, wherein the guide plate socket and the coupling member are configured to lock relative to each other without assisting fixation; and
    placing the first guide wire in the anatomical feature of the patient, wherein the coupling of the axis guide with the guide plate allows the first guide wire to be located at the anatomical axis of the anatomical feature.

2. The method of claim 1, further comprising decoupling the guide plate and the axis guide from the anatomical feature.

3. The method of claim 1, wherein the anatomical feature is a glenoid or an acetabulum.

4. The method of claim 1, further comprising identifying an anatomical geometry, of an anatomical feature of the patient, wherein the geometry of the anatomical feature includes an anatomical axis.

5. The method of claim 4, further comprising fabricating the model of the anatomical feature including a model geometry, the model geometry corresponding to the anatomical geometry of the anatomical feature of the patient.

6. The method of claim 4, wherein identifying the anatomical geometry of the anatomical feature includes determining the anatomical geometry by performing medical imaging of the anatomical feature, the medical imaging including x-ray, magnetic resonance imaging, computed tomography scan, or ultrasound.

7. The method of claim 1, further comprising marking a first indicator on the model at a first location and marking a second indicator on the anatomical feature at a second location, wherein the first location corresponds with the second location.

8. The method of claim 7, further comprising aligning one or more alignment indicia of the guide plate with the first indicator or the second indicator.

9. The method of claim 1, wherein the first guide wire bore is configured to allow the first or second guide wire to translate through the guide plate in one or more orientations.

10. The method of claim 1, wherein the second guide wire bore is configured to allow the first or second guide wire to translate through the axis guide in a single orientation.

11. The method of claim 1, wherein the axis guide is configured to couple with the guide plate at one or more orientations.

12. A guide wire placement apparatus, comprising:
a guide plate including:
   a first guide plate surface configured to couple with an anatomical feature of a patient;
   a second guide plate surface opposite the first guide plate surface, a guide plate socket extending into the first guide plate surface, wherein the guide plate socket includes one or more surface features that are configured to increase the friction coefficient of the guide plate socket; and
   a guide wire bore extending from the guide plate socket to the second guide plate surface to allow a guide wire to translate through the guide plate;
an axis guide comprising:
   a coupling member configured to lock into the guide plate socket in multiple positions; and
   a second guide wire bore passing through the axis guide, wherein the second guide wire bore is configured to allow the guide wire to translate through the second guide wire bore in one position; and
wherein the positionable mating of the coupling member with the guide plate bore aligns the first guide wire bore with the second guide wire bore;
wherein the guide plate socket and the coupling member are configured to lock relative to each other.

13. The apparatus of claim 12, further comprising a model of the anatomical feature configured to mate with the first guide plate surface, wherein the anatomical feature is a scapula or a hip bone.

14. The apparatus of claim 12, wherein the guide plate includes a projection extending transverse to the guide wire bore, and the projection is configured to be aligned with a portion of the anatomical feature to provide orientation of the guide plate relative to the guide wire bore.

15. The apparatus of claim 12, wherein the axis guide includes a handle socket defining a mounting location, and the mounting location used to couple with a handle projecting transverse to the guide wire bore at a fixed angle.

16. The apparatus of claim 12, wherein the guide plate socket is tapered.

17. The apparatus of claim 12, wherein the coupling member is a quasi-spherical body having a plurality of facets, and the one or more surface features are in communication with a surface of the guide plate socket.

18. The apparatus of claim 12, wherein the first guide plate surface includes a plurality of surface protrusions that are configured to penetrate bone to increase the friction coefficient of the first guide plate surface.

19. A guide wire placement apparatus, comprising:
a guide plate including:
   a first guide plate surface configured to couple with an anatomical feature of a patient;
   a second guide plate surface opposite the first guide plate surface, a guide plate socket extending into the first guide plate surface; and
   a guide wire bore extending from the guide plate socket to the second guide plate surface to allow a guide wire to translate through the guide plate;
an axis guide comprising:
   a coupling member configured to lock into the guide plate socket in multiple positions; and
   a second guide wire bore passing through the axis guide, wherein the second guide wire bore is configured to allow the guide wire to translate through the second guide wire bore in one position;
wherein the positionable mating of the coupling member with the guide plate bore aligns the first guide wire bore with the second guide wire bore; and
wherein the guide plate socket and the coupling member are configured to lock relative to each other; and
a model of the anatomical feature configured to mate with the first guide plate surface, wherein the anatomical feature is a scapula or a hip bone.

* * * * *

UNITED STATES PATENT AND TRADEMARK OFFICE
CERTIFICATE OF CORRECTION

PATENT NO.         : 10,925,658 B2
APPLICATION NO.    : 15/956494
DATED              : February 23, 2021
INVENTOR(S)        : Andrew Rolfe Hopkins It is certified that error appears in the above-identified patent and that said Letters Patent is hereby corrected as shown below:

In the Claims

In Column 28, Line 47, in Claim 4, delete "geometry," and insert --geometry-- therefor Signed and Sealed this
Seventh Day of December, 2021

Drew Hirshfeld
*Performing the Functions and Duties of the
Under Secretary of Commerce for Intellectual Property and
Director of the United States Patent and Trademark Office*